(12) United States Patent
Eberl et al.

(10) Patent No.: US 8,042,947 B1
(45) Date of Patent: Oct. 25, 2011

(54) INFORMATION SYSTEM

(75) Inventors: Ronald H. Eberl, Munich-Neuried (DE); Matthias Mayer, legal representative, Munich (DE); Heinrich A. Eberl, Probstried (DE); David Dickerson, Freising (DE); Karsten Koenigstein, Seefeld (DE)

(73) Assignee: metaio GmbH, Munich (DE)

( * ) Notice: Subject to any disclaimer, the term of this patent is extended or adjusted under 35 U.S.C. 154(b) by 1906 days.

(21) Appl. No.: 10/551,650

(22) PCT Filed: Oct. 7, 2000
(Under 37 CFR 1.47)

(86) PCT No.: PCT/EP00/09843
§ 371 (c)(1),
(2), (4) Date: Oct. 5, 2009

(87) PCT Pub. No.: WO02/31580
PCT Pub. Date: Apr. 18, 2002

(51) Int. Cl.
*A61B 3/00* (2006.01)

(52) U.S. Cl. ...................................................... 351/246

(58) Field of Classification Search .................. 351/246, 351/221, 210, 206; 396/51
See application file for complete search history.

(56) References Cited

U.S. PATENT DOCUMENTS 5,815,741 A * 9/1998 Okuyama et al. ............... 396/51
6,227,667 B1   5/2001 Halldorsson et al.

FOREIGN PATENT DOCUMENTS

DE   19631414 A1   2/1998
DE   19728890 A1   2/1999

OTHER PUBLICATIONS

International Search Report mailed Jun. 12, 2001.

* cited by examiner

*Primary Examiner* — Hung Dang
(74) *Attorney, Agent, or Firm* — Crowell & Moring LLP

(57) ABSTRACT

The invention relates to an information system comprising a signal detection device (1751) which detects signals reflected back by at least one eye having a retina; a visual field detection device which detects visible light in a visual field associated with the retina, without detecting a ghost image of the retina; an information device; and an output device which co-operates with the information device to provide information according to the detected light and in correlation with the detected signals.

16 Claims, 18 Drawing Sheets

INFORMATION SYSTEM

FIELD OF THE INVENTION

Figure 1:
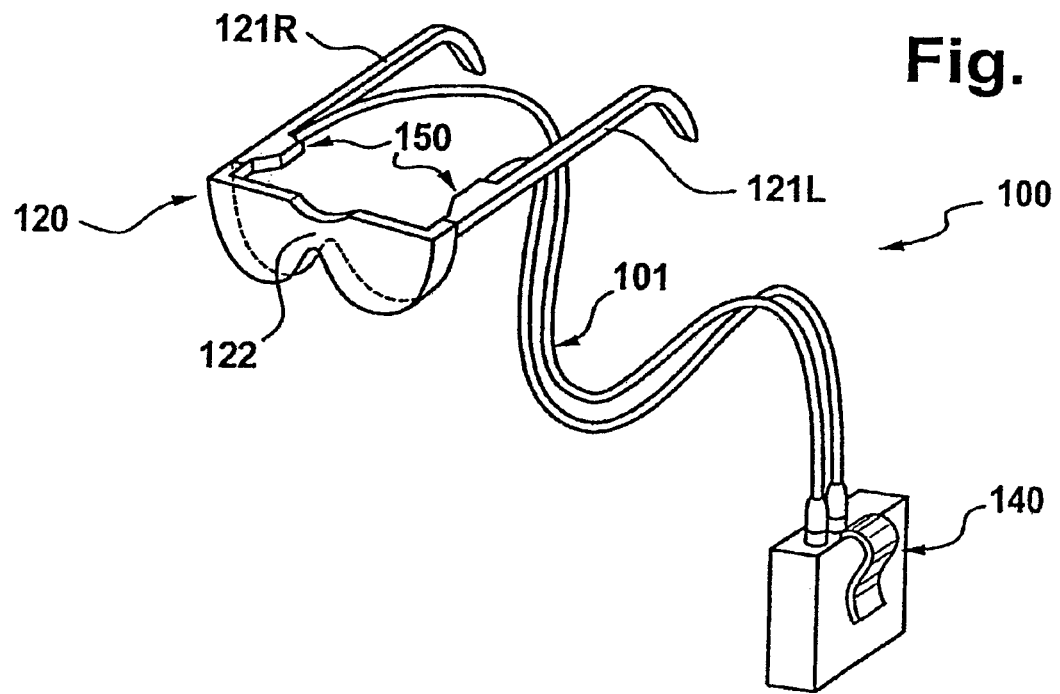

The invention relates to an information system on the basis of a field-of-view capturing apparatus that captures visible light from the naturally perceived field of view of an eye and a corresponding method for the provision of information.

RELATED APPLICATIONS

Optical apparatuses are known from the German laid-open publications DE 196 31 414 A1 and DE 197 28 890 that allow that capture of the retinal reflex image and a superimposition of supplementary images in the eye. In two German patent applications whose filing date and application agree with those of this application, both further embodiments of this optical apparatus as well as systems are described that complement or even replace these apparatuses. In particular, the adjustment of the aforementioned optical apparatus as well as a system are described therein that is also capable, in a novel manner, of projecting images onto an eye. The latter system is based on a projection of an image onto the retina of the eye that is carried out contemporaneously, yet retarded relative to a scan-like capture of the retinal reflex image.

Since the apparatuses and systems described in the aforementioned applications are preferably embodied in the shape of spectacles, they will also be designated hereinafter, for the sake of simplicity, as a spectacle system. This designation does not imply a limitation. Self-evidently, other embodiments of such apparatuses and systems are also equally applicable in the context described hereinbelow in lieu of the "spectacle system."

In DE 196 31 414 A1, numerous possible applications of the spectacle system disclosed therein are discussed without these being described in detail. A co-inventor of the original spectacle system has now examined the possible applications of the aforementioned spectacle system in cooperation with a research team. Further embodiments and alterations of the previously disclosed spectacle systems have resulted from considerations re economical implementability that are to be filed in the context of this and two further patent applications having the same filing date and the same applicant. System features developed by the research team that appear in many of the described embodiments are, inter alia, that the system:

- at least partially captures a cornea reflex image of the eye;
- directs a part of the light falling onto the eye into a sensor apparatus by means of the spherical or spherical-acting reflection layer;
- determines the retinal image via the degree of oxidation of the retinal cones and/or the retinal rods;
- carries out solely a partial capture of a retinal reflex image; and/or
- comprises a field-of-view capturing apparatus that captures visible light from the naturally perceived field of view without capturing a retinal reflex image.

For the sake procedural economy, the content of these three applications was not divided according to these system features. Instead, each of these three applications relates to a respective, combined fundamental concept. These are:

- the embodiment of the spectacle system as an information system that provides information as a function of a naturally perceived field of view of a person;
- the embodiment of the spectacle system as an information system that provides information as a function of signals captured from an eye, yet does not project these into the eye from which the signals were captured; and
- the embodiment of the spectacle system as an information system that provides information as a function of signals captured from an eye, wherein the information is at least partially projected into the eye, the signals, however, are not captured in the manner known from DE 196 31 414 A1.

It should be noted that many applications of the conceived spectacle systems are based on a combination of several of the aforementioned fundamental concepts, the result of which is a natural interrelationship of the associated three applications. Accordingly, there is a certain redundancy between these three applications. With regard to detailed questions relating primarily to only one of the system concepts, however, reference is herewith explicitly made to the application relating to this fundamental concept.

PRIOR ART/TECHNICAL BACKGROUND

Many cases are known from daily life in which it would be useful and/or desirable to have immediate access to information that goes beyond our personal knowledge and sensory impressions. Examples of this are searching for an electrical cable under the plaster in a wall, navigating in a unfamiliar city, collecting wild mushrooms and inspecting a possibly dangerous object by means of a remote-controlled robot.

The strong dependency of a person having vision on their visual senses clearly contributes to the difficulty of providing additional information. Indeed, the fact that people having vision primarily use their eyes makes it necessary, in many cases, to either input the supplementary information via the eyes or to determine the supplementary information based on the information seen. In the case of input via the eyes, however, the orientation of the eyes must be taken into exact consideration for correct "placement" of the input information and to avoid a "jittering" or "blurring" thereof. In addition, in many cases the information should be made available without a controlled movement of the eyeballs; a car driver may have a map on his lap but would prefer not to have to look away from the street.

Due to their dependency on solid media, e.g. paper, CRT and LCD screens, etc., prior visual information systems have not been in a position to sufficiently fulfill the comfort needs of a person having vision. Non-visual information systems previously lacked the correlation to that which is seen that is natural for people having vision.

DE 196 31 414 A1, whose introduction describes several modern information system, in particular from the military field, contains further information to the prior art.

SUMMARY OF THE INVENTION

It is an object of the invention to provide an information system whose presentation of information fulfills the natural needs of person having vision in a previously unachieved manner. It is a further object of the invention to provide an information system of this type that is improved over the prior art with regard to its implementability and economy. It is also an object of the invention to provide corresponding methods for providing information.

In accordance with the invention, this object is achieved through the information system in accordance with claim 1 and the method for providing information in accordance with claim 13. Preferred embodiments of the invention are described in the dependent claims.

In its most general form, the information system in accordance with the invention comprises a signal capturing apparatus that captures signals reflected back from an eye comprising a retina, an information apparatus and an output apparatus that provides, in cooperation with the information apparatus, information in correlation with the captured signals. Preferably, the information is provided as a function of the captured signals and/or as a function of visible light captured from the naturally perceived field of view.

Preferably, one of the aforementioned spectacle systems in which a scanning detection apparatus at least partially captures a retinal reflex image of the retina serves as a signal capturing apparatus. A modification of this detection apparatus that captures light reflected on a cornea of the eye in lieu of the retinal reflex image is particularly advantageous for infrared applications since the cornea strongly reflects light having a wavelength of roughly 1.1 μm. It is also fundamentally possible to make correspondingly valuable statements about the image falling onto the retina by capturing the chemical change of the rods and/or cones.

The inventors of this invention have also determined that a capturing of the field of view complementary to the capturing of signals reflected back from the eye has particular advantages. For the purpose of such a complementary capturing, the field-of-view capturing apparatus and/or the information apparatus of the information system in accordance with the invention preferably comprises a spherical or spherical-acting reflection layer that is positioned essentially confocal to the eye that deflects a part of the light directed onto the eye into a sensor apparatus for capture. Due to the fact that the reflectivity of the reflective layer is several times higher than that of the retinal or corneal reflex, considerably more light can be captured using equally sensitive photo-sensors. Moreover, correspondingly cheap photo-sensors could be used in the sensor apparatus. It can also be advantageous if the light falling onto the eye is not solely, only partially or not at all captured via the retinal reflex.

Depending on the intended application, not all spatial regions of the field of view must be captured. In an application, for example, in which supplementary information with regard to an object upon which the eye has fixed its gaze is provided by an information system in accordance with the invention, it could be sufficient to capture the light falling onto the fovea and to subject it to a pattern detection or other type of analysis since an object upon which the eye has fixed its gaze is typically imaged on the fovea which represents the area of keenest sight. Accordingly, capturing the light that falls onto this part of the retina would possibly be sufficient to determine a sufficient number of characterizing object features.

It is also sensible if only a limited spectral range of the light falling onto the eye is detected. If, for example, the infrared light falling onto an eye is detected, the orientation of the eye and/or valuable information from the field of view can be determined, even at night.

Accordingly, any limitations with regard to the capturing of the light falling onto an eye can be meaningful. In particular, limitations of the captured spectral range, the captured regions of the field of view and/or the captured time spans of vision are applied as necessary.

For the purpose of redundant or stereoscopic image capture, the correspond apparatus of the information system in accordance with the invention can be designed so as to capture the light falling onto several eyes. Depending on the field of application, the eyes must not necessarily belong to a single person. For example, it would be possible to display the images perceived by the eyes of several firemen onto monitors in a command center in addition to position and fire strength information determined from an infrared spectral analysis of the images.

In the field of ophthalmology, a distinction is made between the terms "field of view" and "field of vision." A field of view is the part of a space that can be seen with a stationary eye. A Field of vision is the region that can be seen with the eyes. Consequently, here, as elsewhere, the field of view is to be understood as the cause of the light that naturally falls onto an eye.

The Capture of the Field of View

Due to the incorporation of a field-of-view capturing apparatus, the information system is capable of capturing visible light from the field of view associated with the eye of a quality, i.e. with a sensitivity, a resolution, a sharpness, etc. that far exceeds the natural visual acuity of the eye. In addition, on account of the correlation in accordance with the invention of the provision of information with the signals captured by the signal capturing apparatus, it is possible to treat corresponding parts of the captured light during a processing that occurs in the course of the provision of information as if they were reflex images captured from the eye, i.e. as if they were that which is truly seen. Such an embodiment of the information system in accordance with the invention thus combines the advantages of an information system that obtains high quality field of view information directly from the field of view with the advantages of an information system that obtains the truly seen field of view information from the eye.

The correlation of the presentation of information with the captured signals reflected back from the eye can be carried out, for example, by capturing several pixels of an ocular reflex image, e.g. a cornea or retinal reflex image, that are brought into connection with corresponding pixels from the captured field of view via an evaluation apparatus. A gaze direction of the eye determined via the captured signals can also serve to establish a correlation between the field of view information obtained from the captured field of view and that which is truly seen. As will be described hereinbelow, the correlation can, however, also comprise projecting obtained field of view information onto the retina in a correlated manner to that which is seen.

Naturally, the field-of-view capturing apparatus must not be limited to capturing of the field of view, but may also comprise a partial or complete capturing of the field of vision which encompasses an at least partial capturing of the field of view.

The high quality of the image captured from the field of vision and/or field of view can also serve as a basis for an extrasensory presentation of information. For example, field-of-view information can be obtained from the captured light of the field of view and projected onto the retina such that the image seen by the eye seems at least partially sharper, closer, wider angled or in some other manner extrasensory.

The invention is conceived as having an information source that can comprise a data bank, a sensory unit, an information network connection and/or an evaluation apparatus.

A particularly interesting embodiment of the invention comprises a sensory unit as information source since, in this manner, an extrasensory perception can be brought into connection with that which is seen. In the cited example of searching for an electric cable, the information source in accordance with the invention could be magnetic field sensors that are capable of localizing metallic cables with regard to a known coordinate system, e.g. the captured field of view. It would thus be possible, for example by means of suitable image processing software, to superimpose the run of existing electrical cables by means of a projection of a supplementary image as described in aforementioned patent applications onto the image seen by the eye.

Any type of known sensor is suitable for use as an information source, in particular when the sensor is activated and/or queried on the basis of the captured light image. During inspection of an integrated electronic circuit, for example, the position of a conductor on a manufactured chip could be computed after a directed gaze at that conductor on a circuit plan of the circuit and the pressing of a button so that the current and voltage values of the conductor are determined by means of the non-contacting measuring device and presented to the use via the spectacle system.

An example of an information system comprising a data bank and an information, network connection is an intracompany mail distribution system in which files are provided with bar code stickers that uniquely identify the respective file. If a file is to be sent within the company, the sender enters e.g. the receiver's extension and a code designating the file by means of software that correspondingly stores these data in a data bank in one of the many known ways. When the file is later sorted, the identifying bar code is captured via the spectacle system worn by a mail distribution employee, e.g. via a directed gaze and a push of a button, and recognized via a recognition apparatus or recognition software. The data associated with the file relevant to mail distribution are retrieved from the data bank via a radio connection to an intra-company data network and these data are presented to the mail distribution employee, after pre-processing, if necessary, via a suitable output apparatus, e.g. as an announcement via headphones "Mr. Schmidt, finance department, building G, second floor, room 310."

The term "evaluation apparatus" is to be understood as any type of evaluation apparatus, in particular image processing apparatuses. Such evaluation apparatuses were also discussed in the examples above.

In accordance with the invention, the information can be provided tactually, visually, audibly, smellably and/or tastably. It is an object of the invention to allow a presentation of information that complies with the needs of a person having vision in a manner not previously achieved. This can comprise providing the information to the person in a suitable manner, i.e. using one or more of the five senses. The information can, however, be presented in an arbitrary manner and does not require a particular addressee. For example, the information can be provided to a further system or radiated into the environment via an optical or acoustic output apparatus. The claimed dependency between the provision of information and the light image falling onto the eye guarantees that the correlation that a person having vision expects exists between the information provided and that which is seen.

This dependency is taken into consideration by the apparatus in accordance with the invention during the determination of the information, during the provision of the information or during both of these inherent processes. Examples for establishing this dependency during the determination of the information are given above. During the provision of information, this dependency can be established, for example, by blending the information into the image seen by projecting back into the eye in such a way that a temporal, spectral, spatial, contrastual or other sensible correlation is established between the information and the image seen. In particular, the dependency can consist of the captured light image being used to determine the position and orientation of the eyeball so that an image projected onto the eye for the sake of providing the information appears to stand still during a motion of the eye, appears to move with the eye during a motion of the eye or appears to move in accordance with a predetermined course during a motion of the eye. In particular, the effect of the saccadic motion of the eye on these processes can be taken into consideration and/or compensated.

Naturally, the information must not necessarily be provided to a person, but can also be provided to another system.

Tracking

With the information system in accordance with the invention, it is thus possible to determine the position and orientation of at least one eye quickly, accurately and at little expense, e.g. at a determining rate of 100 Hz, a positional accuracy of several micrometers and using a portably constructed apparatus. By using the information system in accordance with the invention during the dynamic evaluation of the orientation of the eye, the processing can be carried out so quickly that the accuracy is not impaired by the saccadic motion of the eye. This is achieved in that the information system comprises a signal capturing apparatus that does not contact the eye and the captures signals reflected back from the eye. Reflectable signals, e.g. sound or electromagnetic signals, allow a high frequency capturing such that the processing speed is primarily determined by an evaluation apparatus comprised by the information system. In the field of signal processing hardware, however, considerable progress has been made in the last few years with regard to processing speed, power consumption and system size. The inventor's research has revealed that an information system can achieve the strived-for processing speed through such a design.

Typically, a part of the information system itself serves as a reference coordinate system. However, its is also possible that the information system solely represents an intermediate reference coordinate system in another reference coordinate system and that the relationship between the intermediate reference coordinate system and the reference coordinate system is determined e.g. via the evaluation apparatus or another mechanism.

Preferably, the signal capturing apparatus captures light reflected back from the eye. Light is an excellent medium for transmitting the signals reflected back from the eye since the presence of light is a prerequisite for the ability to use the eye. However, the ocular reflex signal information that results through the reflection on the eye is superimposed with field-of-view signal information transmitted by the light from the field of view. These differing pieces of information, however, can be distinguished through use of known signal processing methods and can be sensibly used for determining the orientation of the eye. This is particularly true when the signal transmission medium is from a signal source belonging to the information system that applies a predetermined signal to the medium prior to its reflection on the eye.

Similarly, the capture of signals from other signal transmission media than light can also be advantageous. Components for generating and capturing sound waves, for example, are commercially available in various cost-efficient and compact forms. Such components can also be implemented as integrated elements of an integrated circuit. Similar considerations apply to the non-visible frequency range of electromagnetic waves.

Although not entirely researched, it is conceivable that an information system with a plurality of signal capturing apparatuses that capture signals from different media or spectral ranges could demonstrate improved system characteristics. This discovery is based on considerations that the evaluation apparatus could also take over other system tasks in the case of underload and that the signal processing carried out by the evaluation apparatus depends strongly on the information content of the signal to be processed. It would thus be advantageous to base the information system on signal capturing that only demands a little performance from the evaluation apparatus for evaluating, but itself might not supply the basis for sufficient accuracy and to complement and/or calibrate this low-processing signal capturing via the results of an accurate and processing-intensive, yet only intermittently executed signal capturing such that the necessary accuracy is achieved at any time.

A capturing of the retinal reflex in which the retinal reflex of natural or artificial light is intermittently or partial captured as the signal reflected back from the eye has turned out to be useful. A full capturing of the retinal reflex is both time consuming and demanding on performance. On the other hand, a capturing of the retinal reflex is useful inasmuch as it allows the relationship of the perceived field of view to the retina to be directly determined. Indeed, as noted above, a processing of the captured retinal reflex allows both retinal features such as e.g. the fovea centralis or the blind spot as well as the reflex image of the light falling onto the eye to be determined. The network of blood vessels present in the choroid coat also becomes visible through appropriate processing of the retinal reflex image, which yields a very good basis for determining the orientation of the eyeball. If the retinal reflex is thus captured intermittently or partially, the processing complexity can be reduced without sacrificing an exact determination of the relationship of the perceived field of view to the retina. Naturally, the retinal features can be followed without capturing the retinal reflex. For example, the blood vessels of the choroid coat can be recognized via their radiation of heat that is visible in the infrared range.

The present invention will be described hereinafter in further detail on the basis of a description of embodiments with reference to the figures. Many features of the invention will be explained in the narrow context of the respective, concretely disclosed embodiment. Naturally, each individual feature of the invention can be combined with any other feature as far as the resulting combination does not lead to a result that the person skilled in the art would immediately recognize as nonsensical. This statement does not affect the determination of the scope of commercial protection of this patent application/patent to the respect that the scope of protection is determined by the claims under applicable law.

Figure 2:
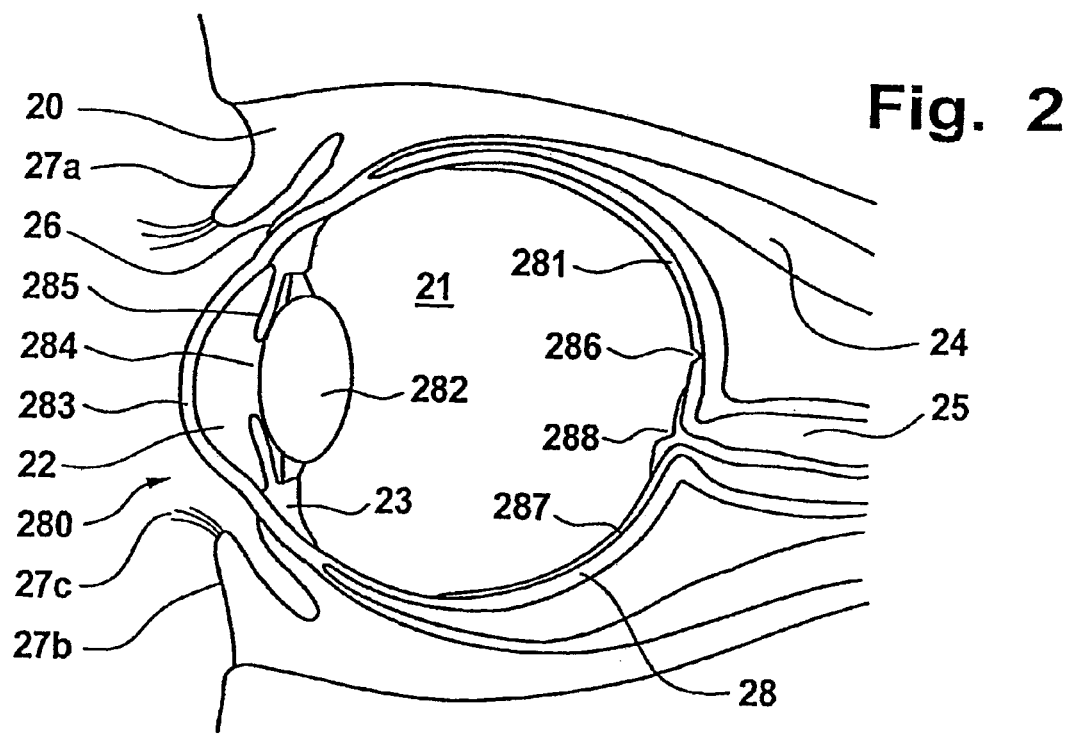
Figure 3:
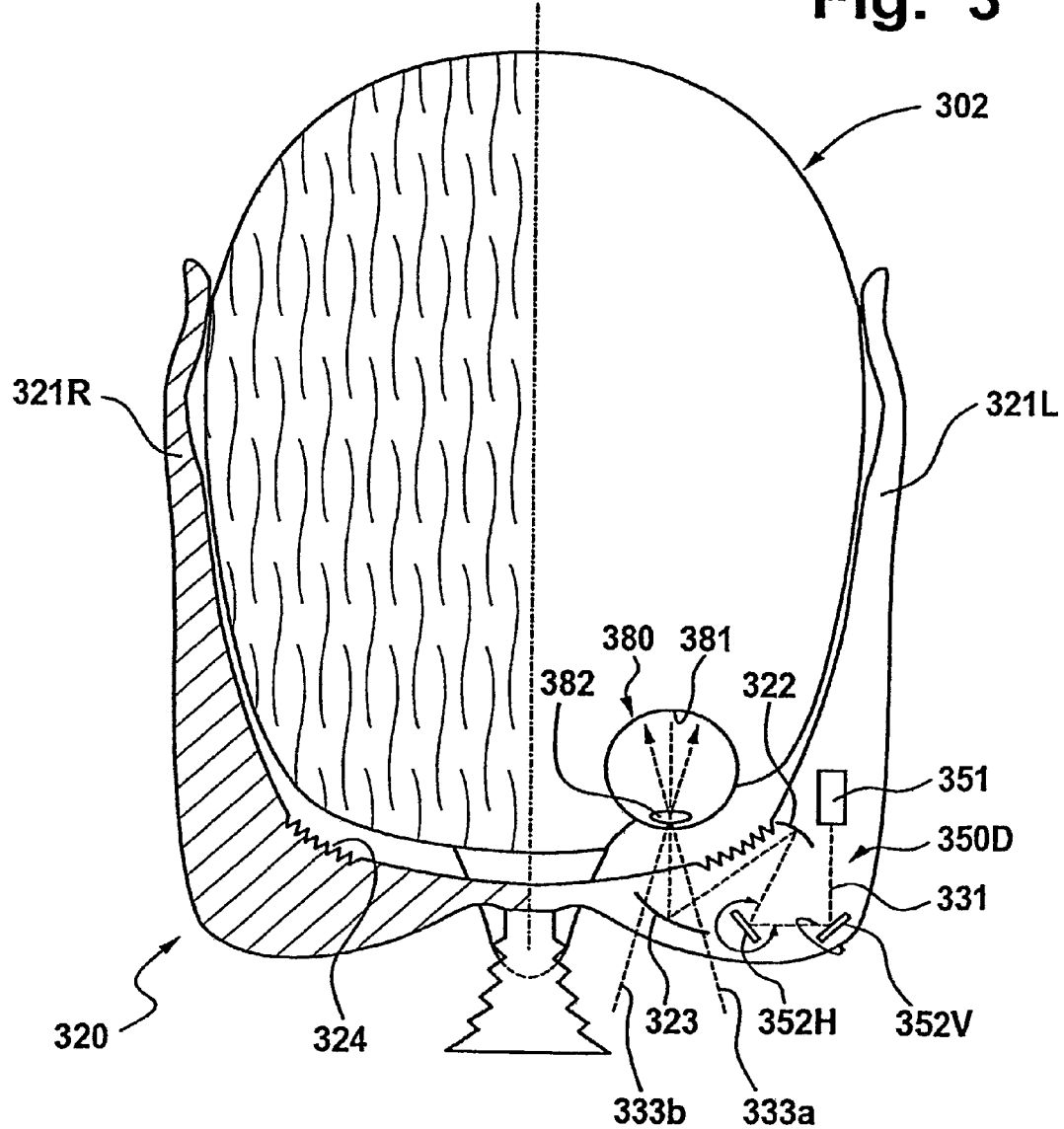
Figure 4:
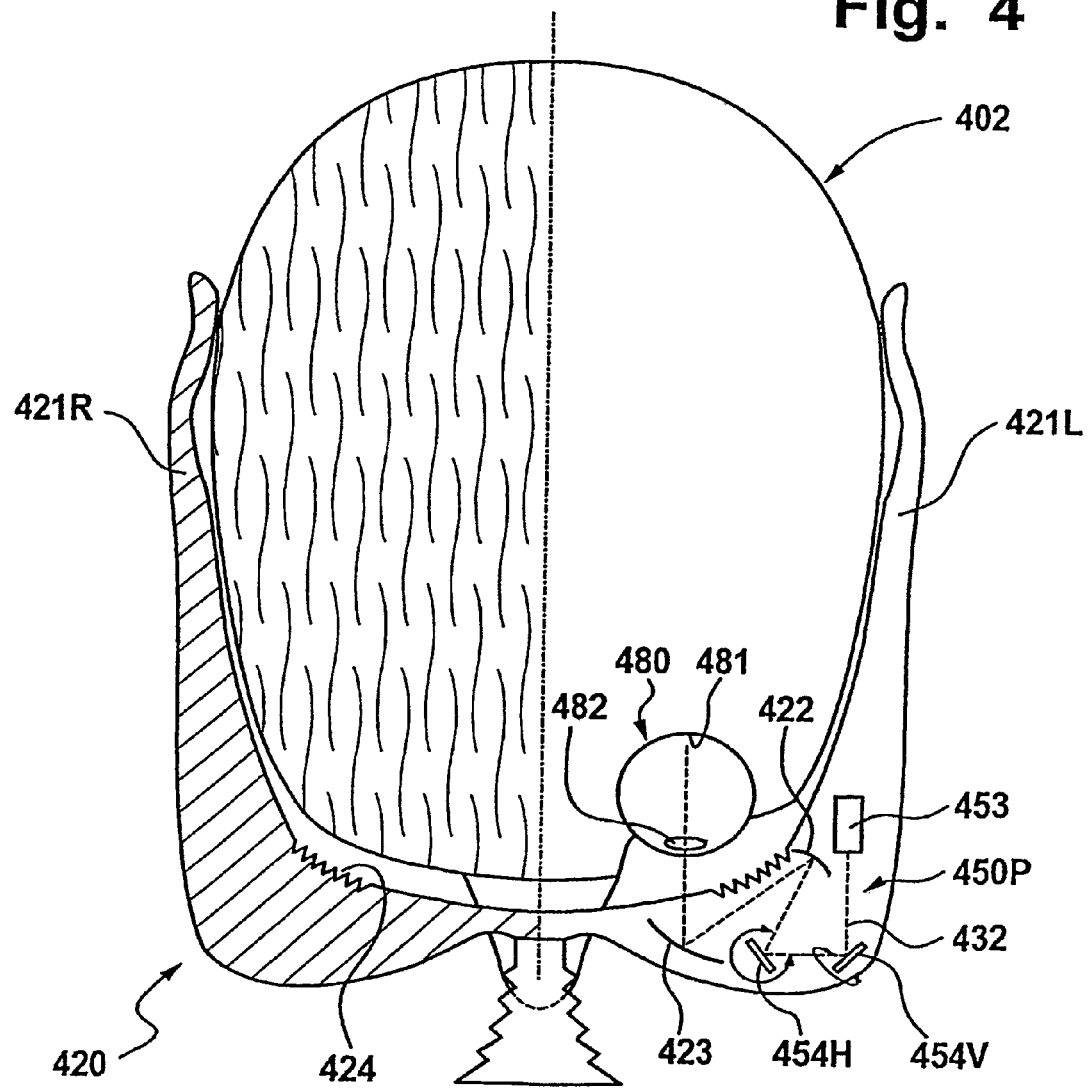
Figure 5A:
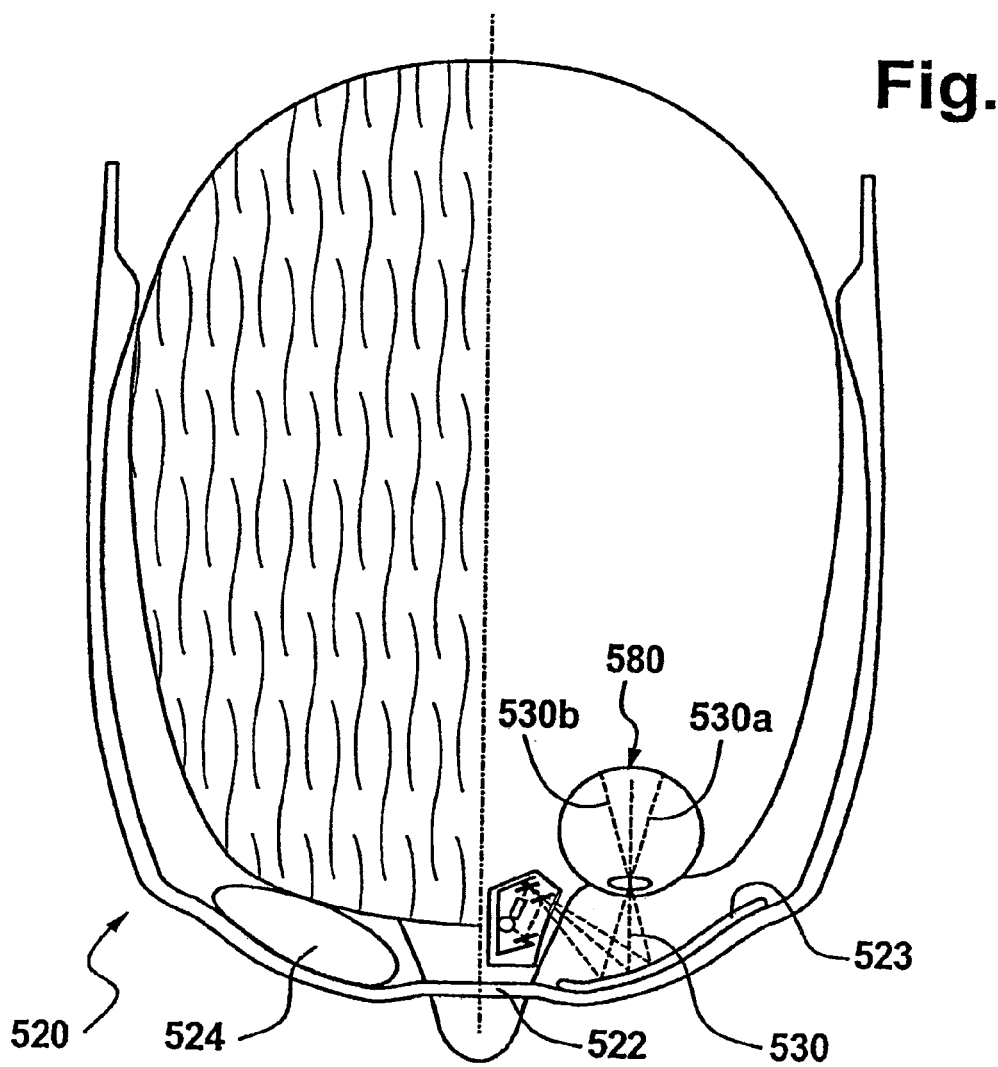
Figure 5B:
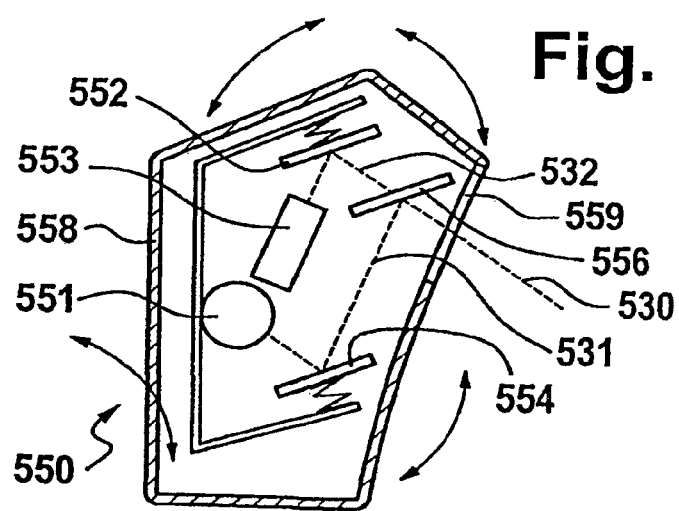
Figure 6A:
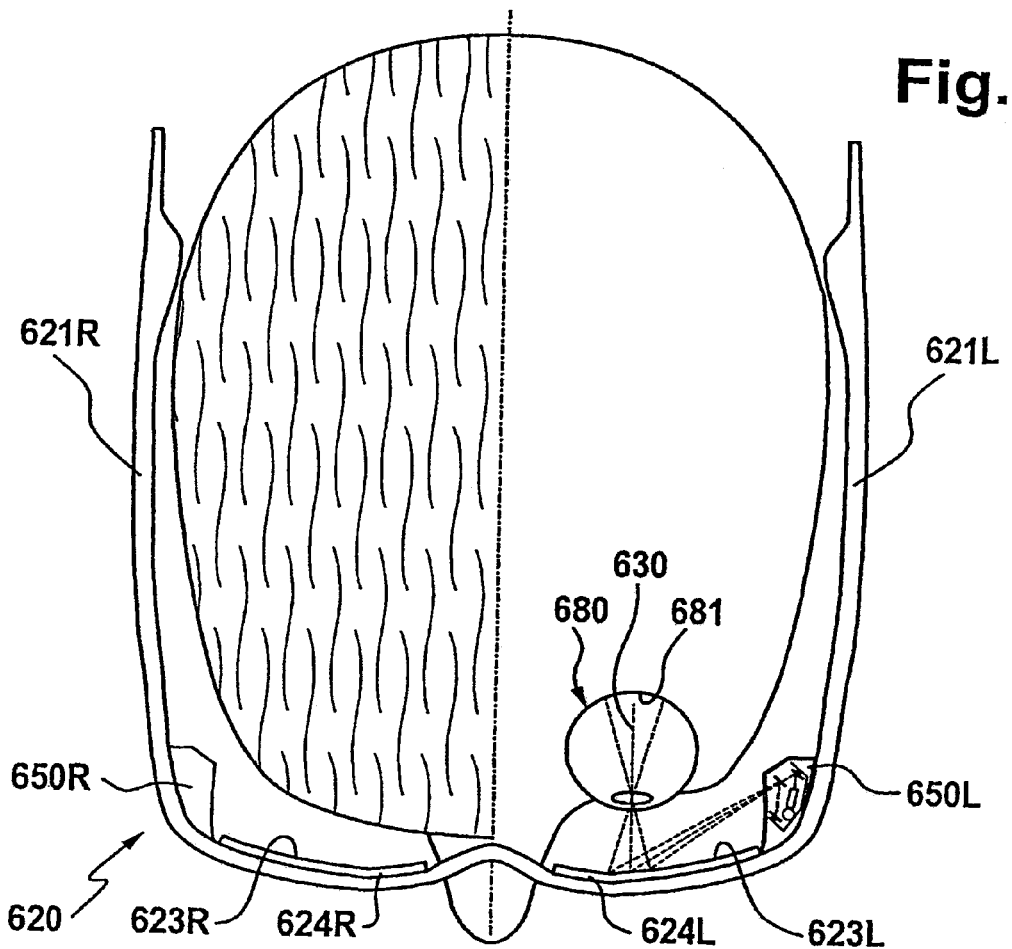
Figure 6B:
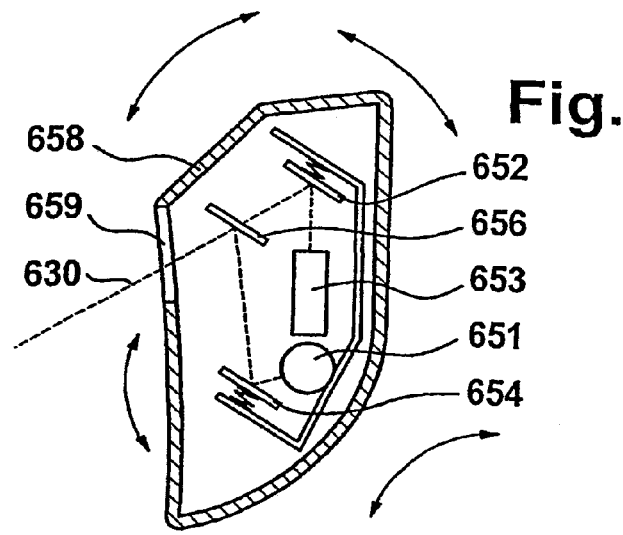
Figure 7A:
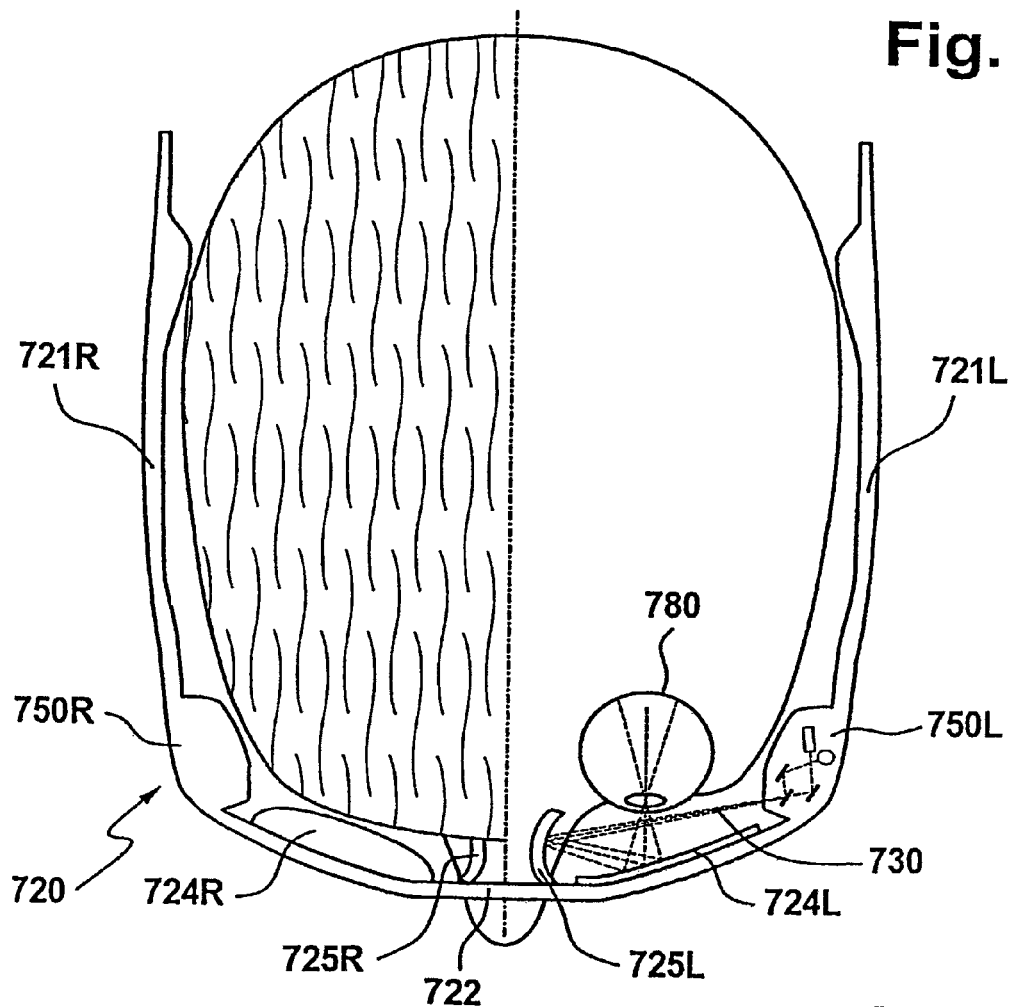
Figure 7B:
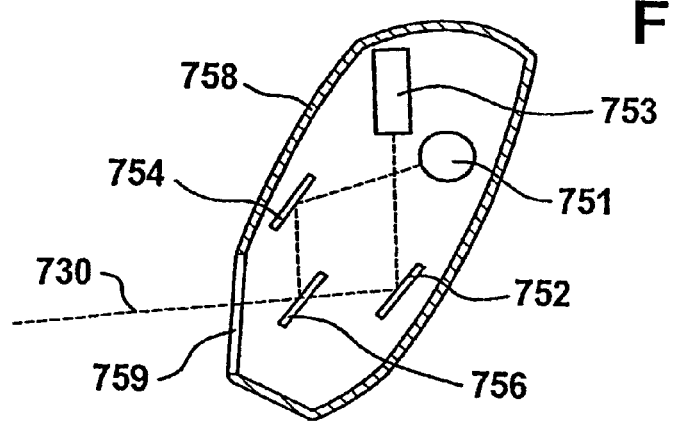
Figure 8:
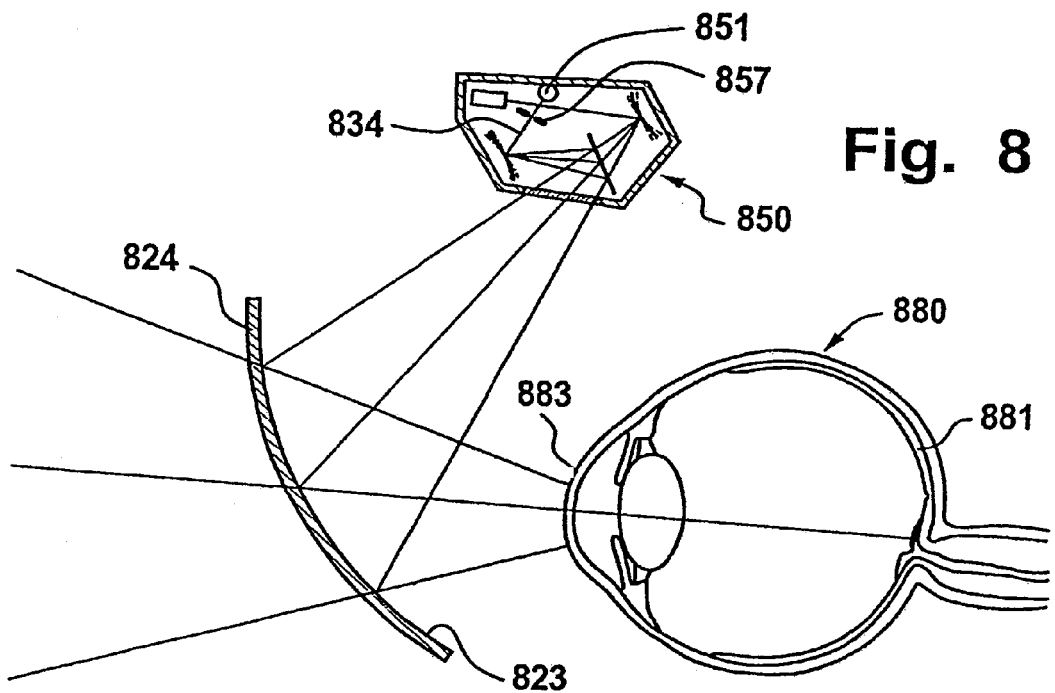
Figure 9:
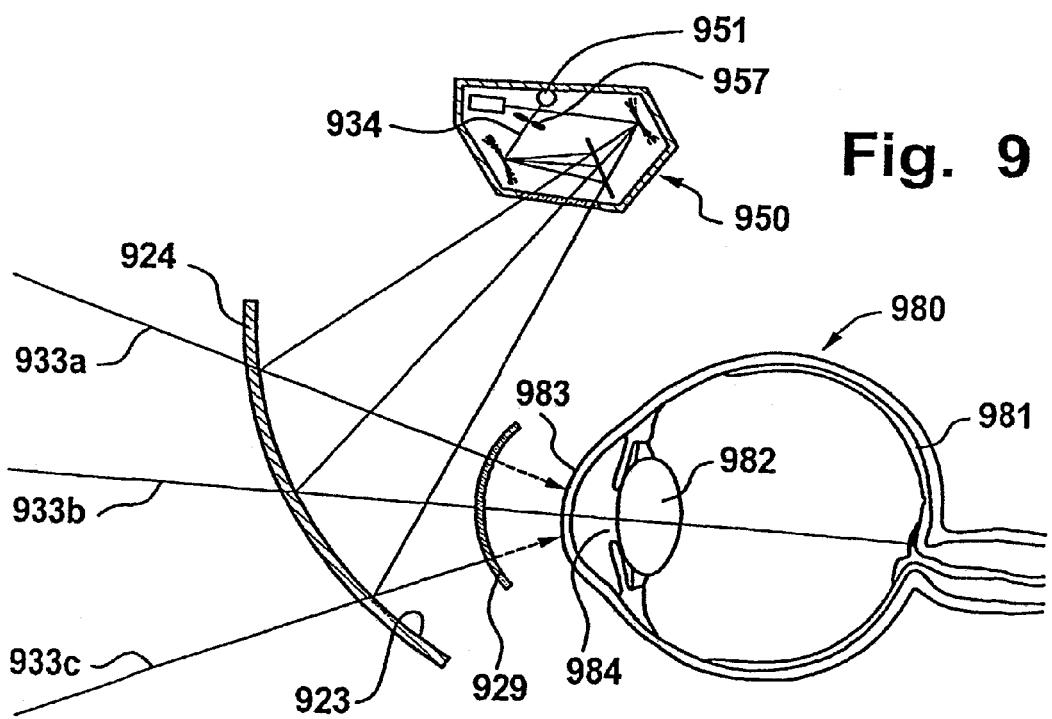
Figure 10A:
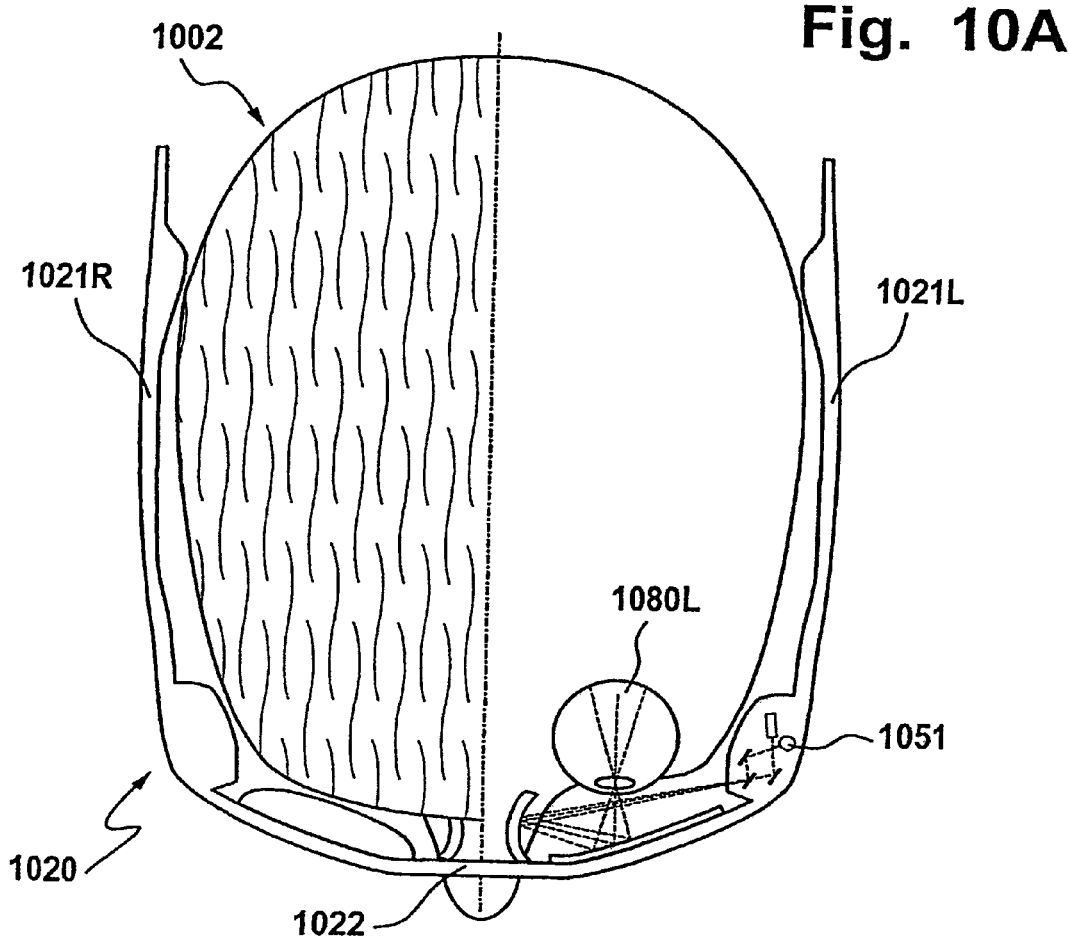
Figure 10B:
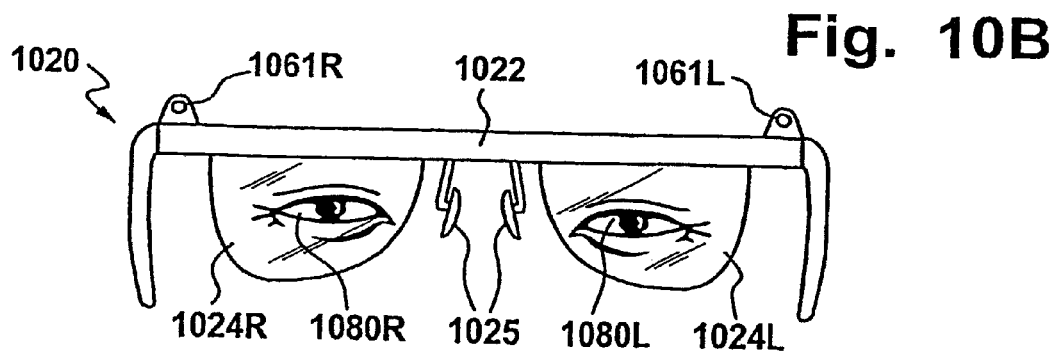
Figure 11A:
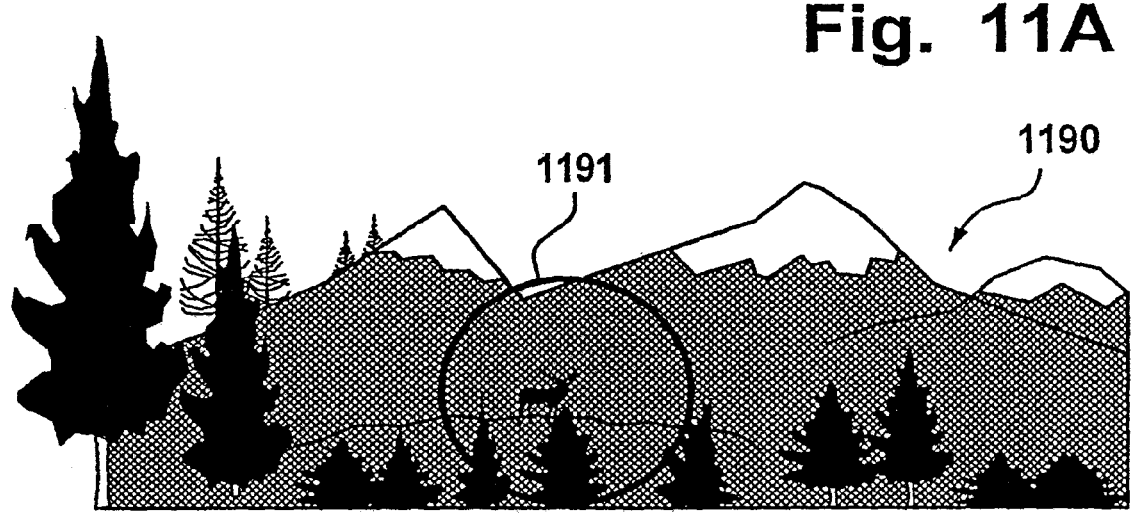
Figure 11B:
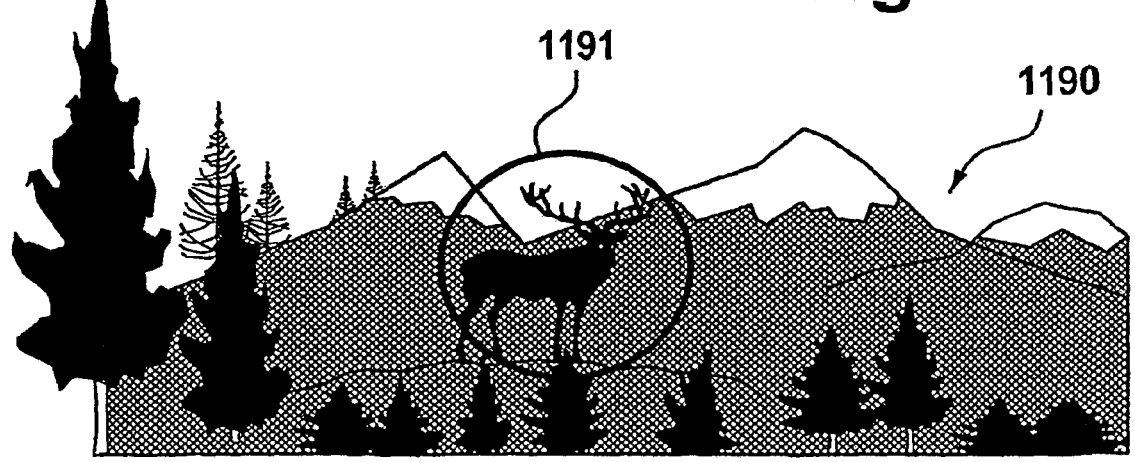
Figure 11C:
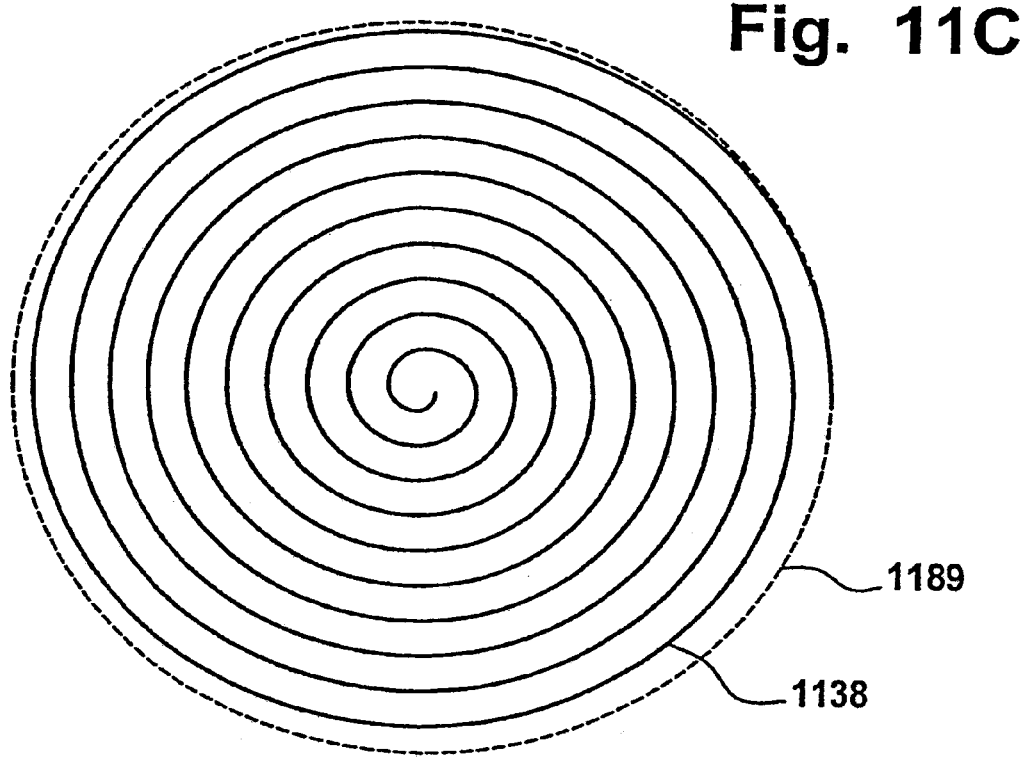
Figure 11D:
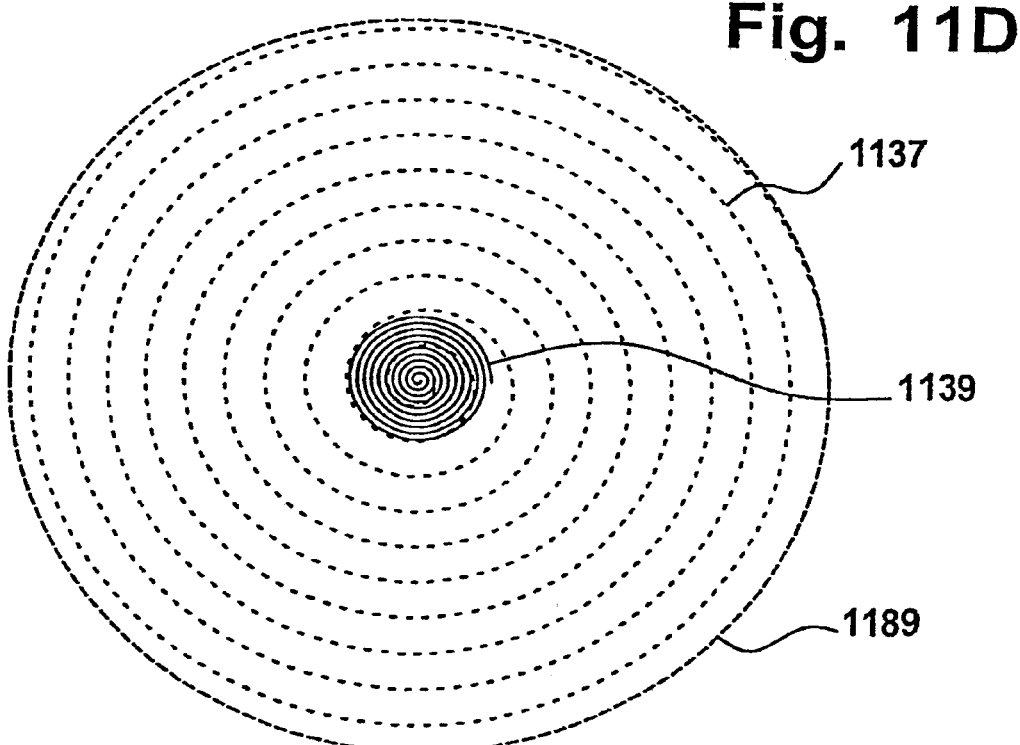
Figure 12A:
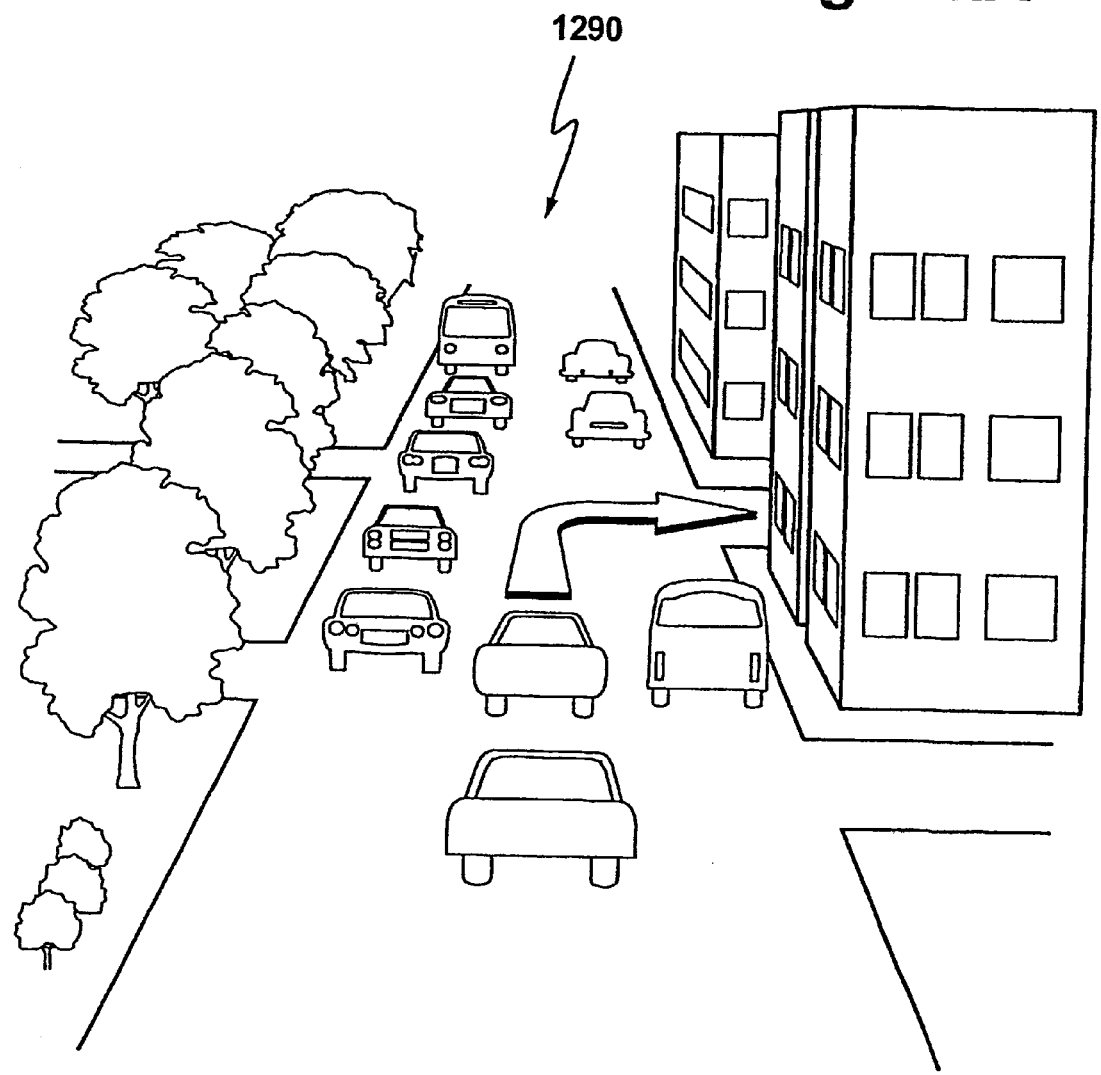
Figure 12B:
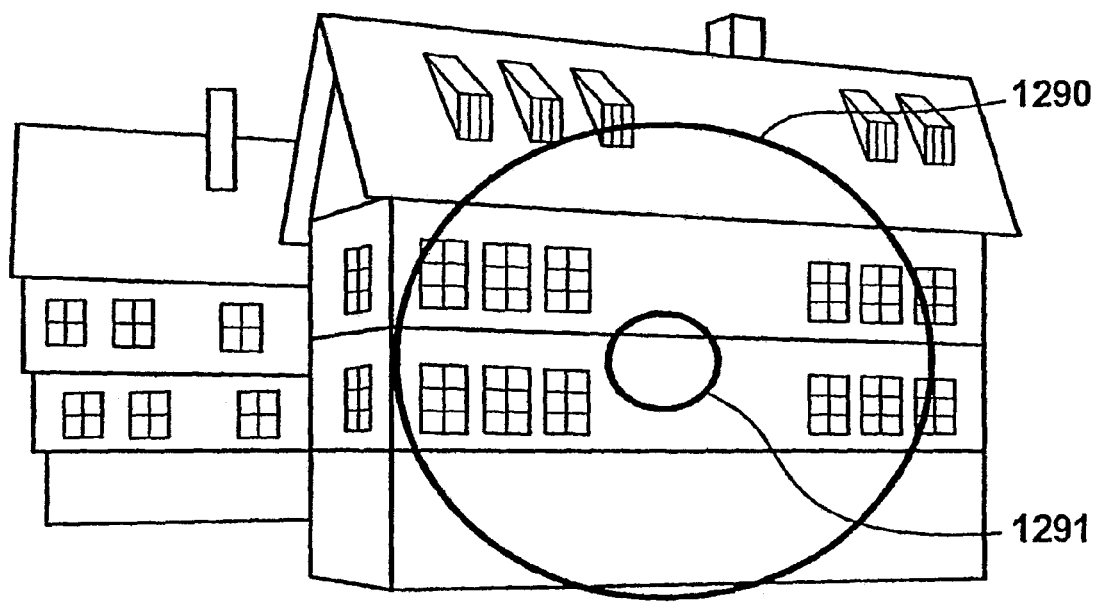
Figure 12C:
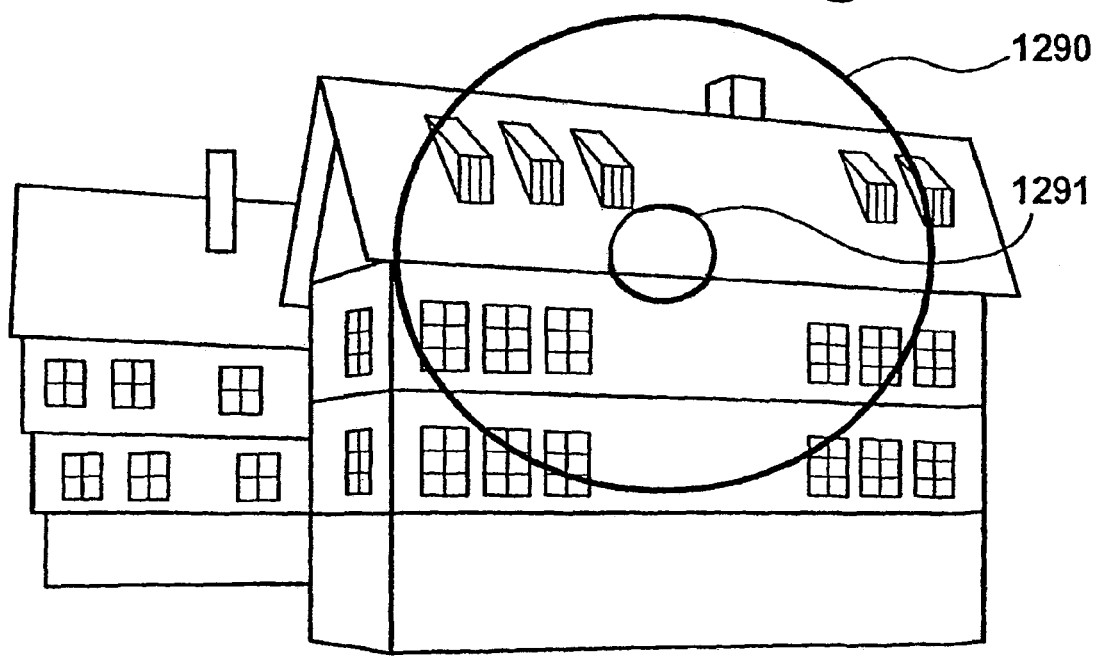
Figure 12D:
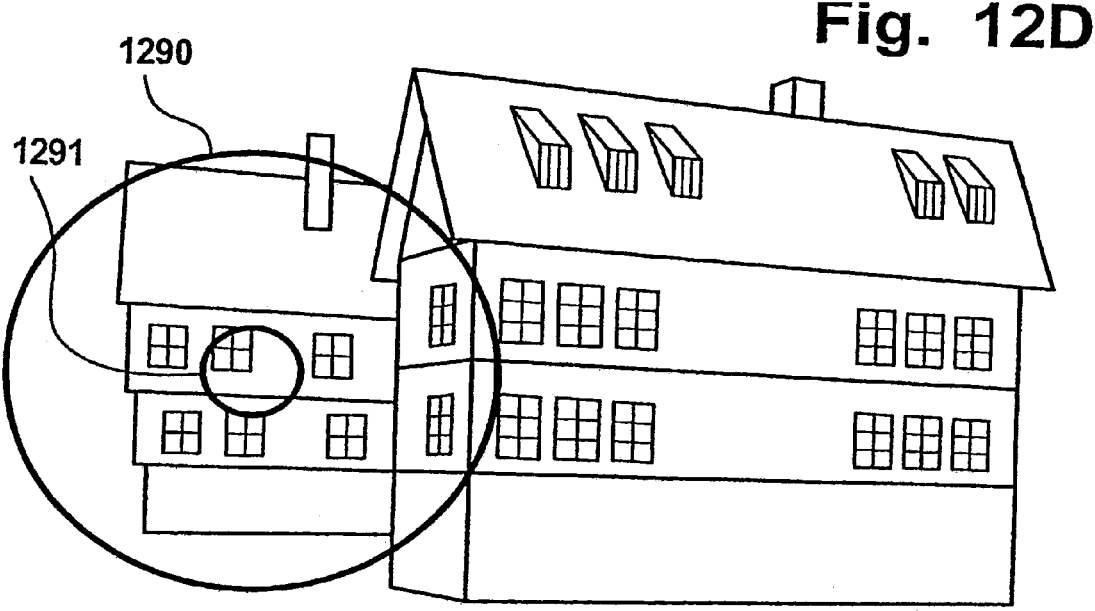
Figure 12E:
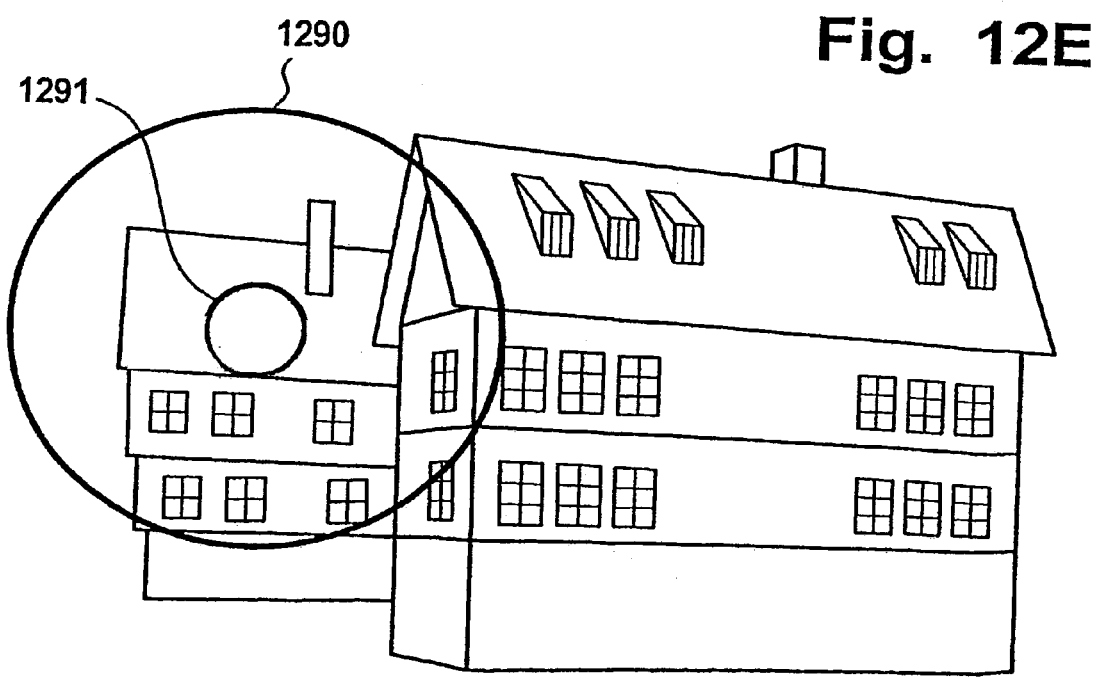
Figure 13A:
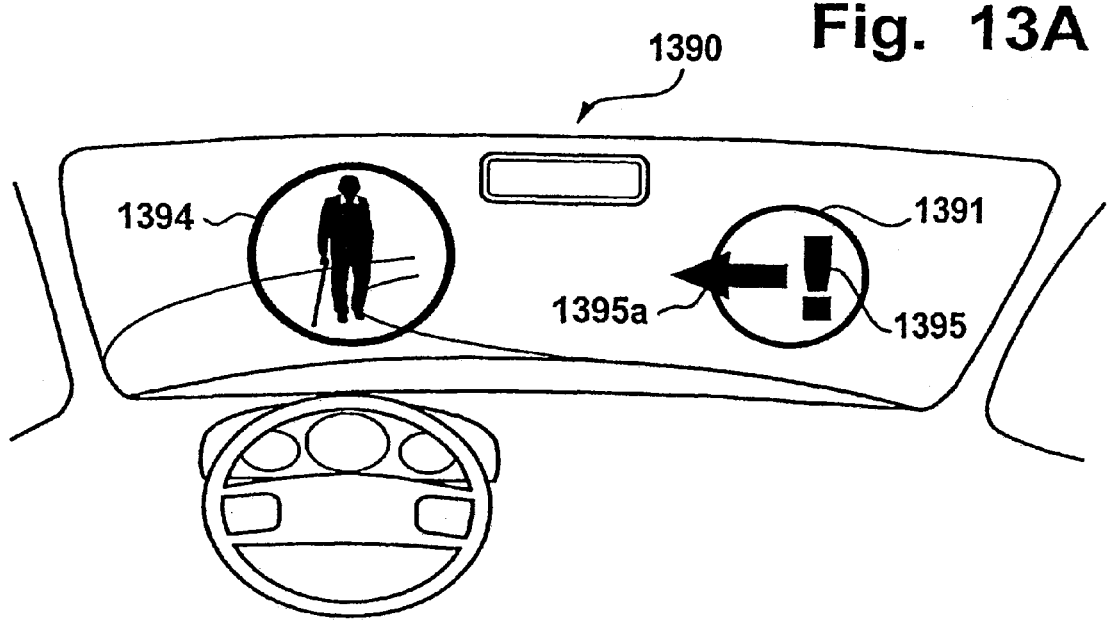
Figure 13B:
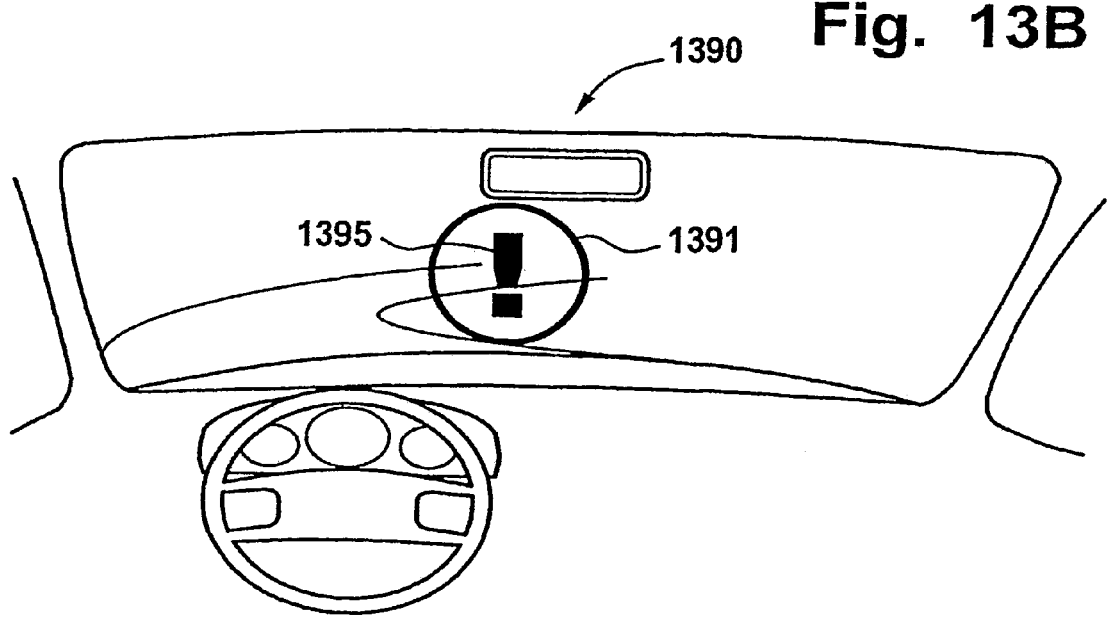
Figure 14A:
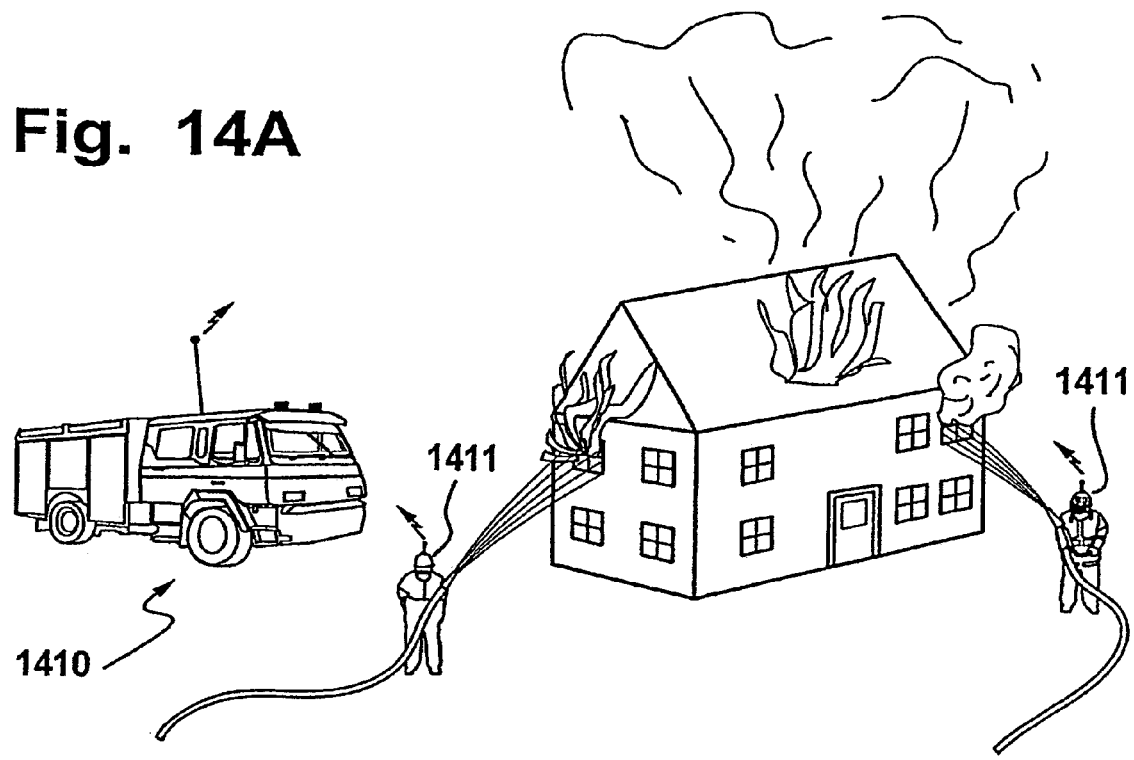
Figure 14B:
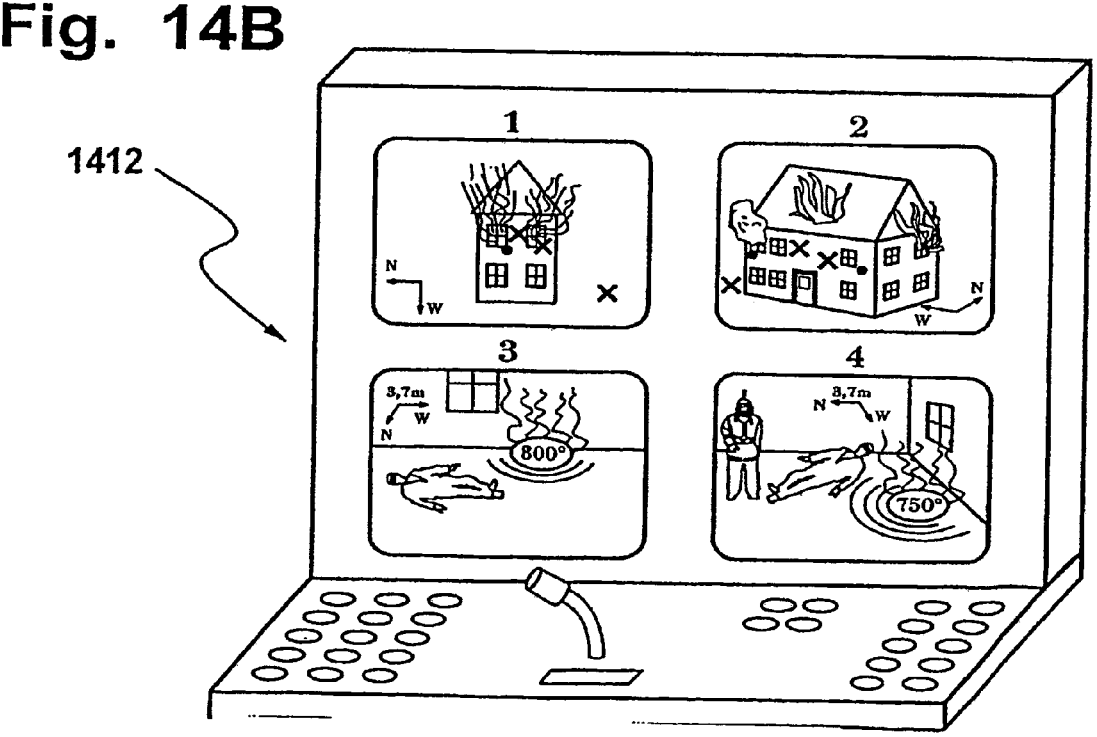
Figure 15:
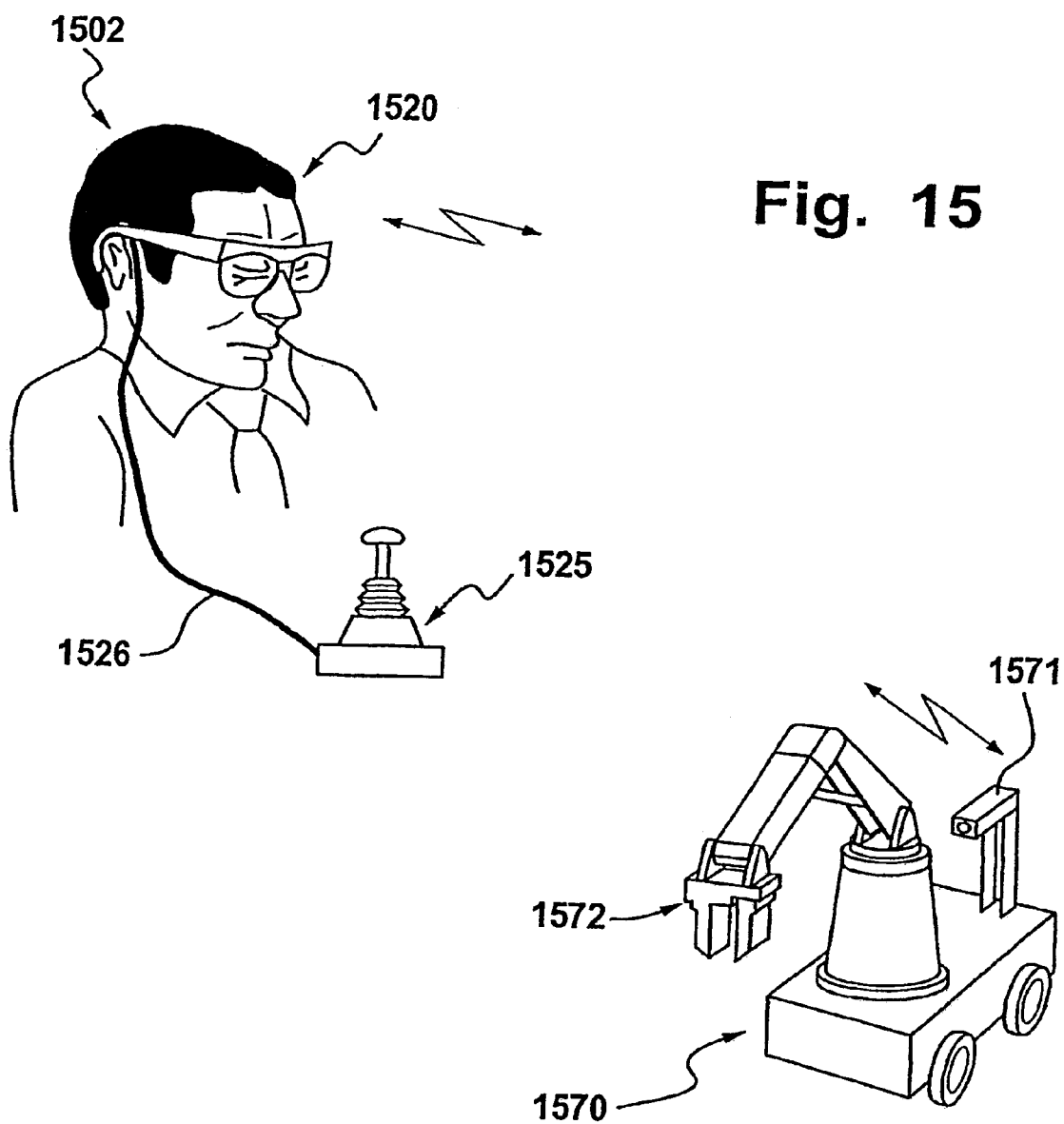
Figure 16:
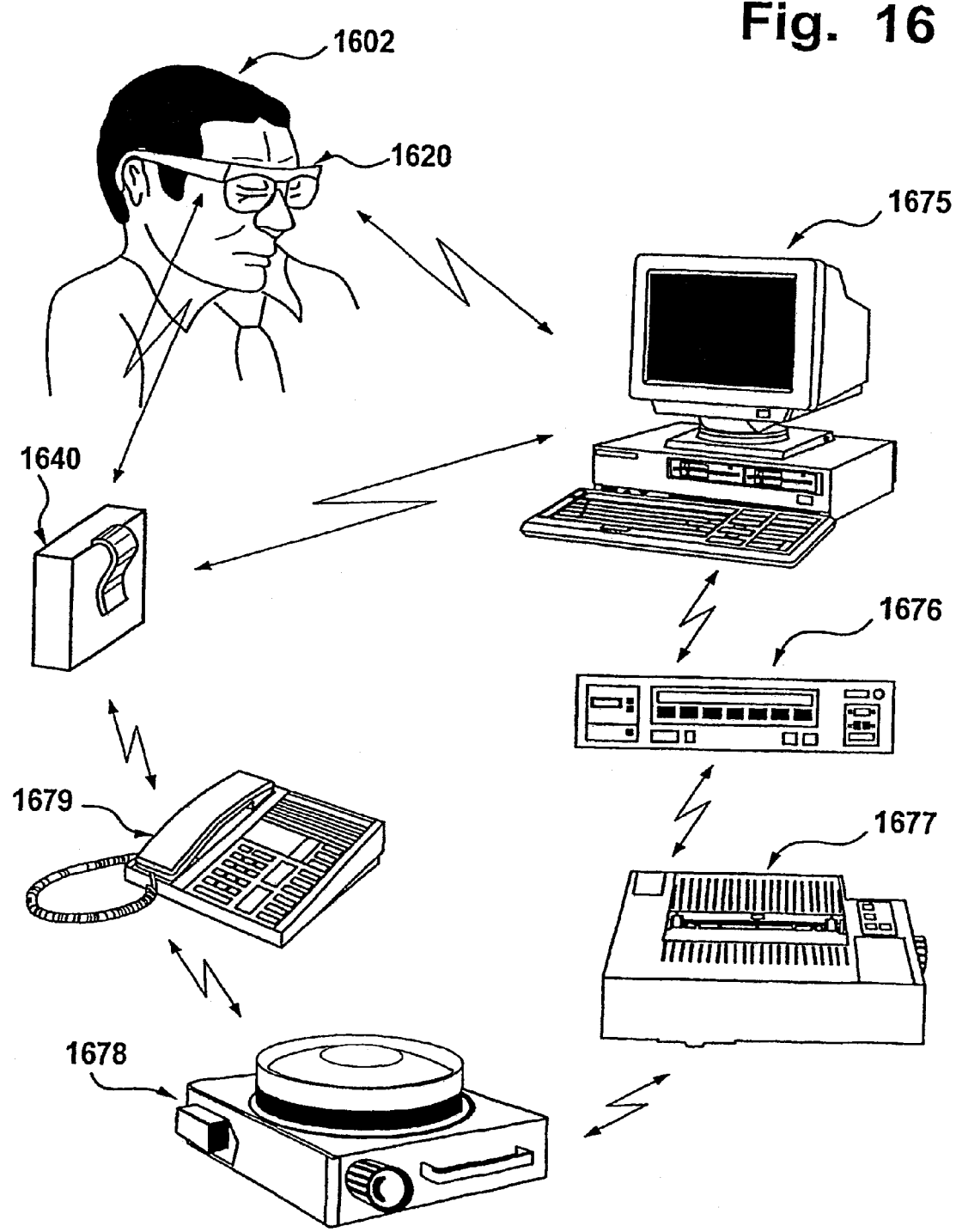
Figure 17:
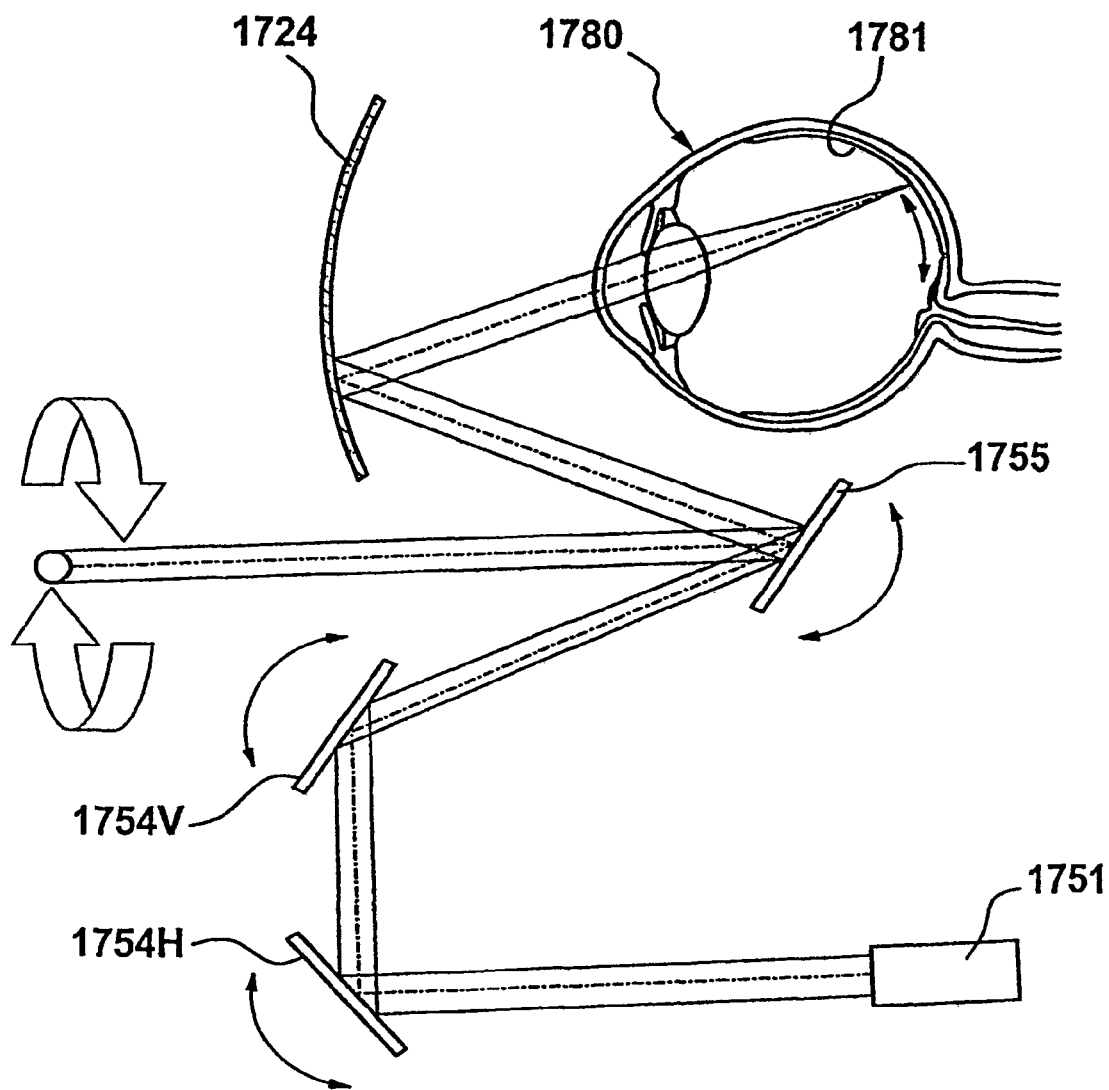

The figures show:

FIG. 1—an information system in accordance with a first embodiment of the invention;

FIG. 2—a detailed view of an eye in cross-section;

FIG. 3—a known embodiment of an interactive spectacle system in which a signal capturing apparatus is provided in the form of a scanning eye detection apparatus;

FIG. 4—a known embodiment of interactive spectacles in which an output apparatus in the form of a scanning projection apparatus is provided;

FIG. 5A—interactive spectacles in accordance with a first embodiment;

FIG. 5B—a detailed drawing of a combined signal capturing and projection apparatus illustrated in FIG. 5;

FIG. 6A—interactive spectacles in accordance with a second embodiment;

FIG. 6B—a detailed drawing of a combined signal capturing and projection apparatus illustrated in FIG. 6A;

FIG. 7A—interactive spectacles in accordance with a third embodiment;

FIG. 7B—a detailed drawing of a combined signal capturing and projection apparatus illustrated in FIG. 7A;

FIG. 8—interactive spectacles in accordance with a fourth embodiment;

FIG. 9—interactive spectacles in accordance with a five embodiment;

FIG. 10A—a plan view of spectacles in accordance with a sixth embodiment;

FIG. 10B—a front view of spectacles in accordance with a sixth embodiment;

FIG. 11A—the naturally perceived field of view of a user of an information system designed in accordance with a seventh embodiment;

FIG. 11B—the naturally perceived field of view of a user of an information system designed in accordance with a seventh embodiment;

FIG. 11C—a schematic representation of a scan pattern;

FIG. 11D—a schematic representation of a modified scan pattern;

FIG. 12A—the naturally perceived field of view of a user of an information system designed in accordance with an eighth embodiment;

FIG. 12B—the naturally perceived field of view of a user of an information system designed in accordance with an eighth embodiment;

FIG. 12C—the naturally perceived field of view of a user of an information system designed in accordance with an eighth embodiment;

FIG. 12D—the naturally perceived field of view of a user of an information system designed in accordance with an eighth embodiment;

FIG. 12E—the naturally perceived field of view of a user of an information system designed in accordance with an eighth embodiment;

FIG. 13A—the naturally perceived field of view of a user of an information system designed in accordance with an ninth embodiment;

FIG. 13B—the naturally perceived field of view of a user of an information system designed in accordance with an ninth embodiment;

FIG. 14A—an information system in accordance with the invention in accordance with a tenth embodiment;

FIG. 14B—an information system in accordance with the invention in accordance with a tenth embodiment;

FIG. 15—an information system in accordance with the invention in accordance with a eleventh embodiment;

FIG. 16—a schematic representation of an information system in accordance with the invention in accordance with a twelfth embodiment; and FIG. 17—an optical system in accordance with a thirteenth embodiment.

In the description of the figures, similar or identical objects are designated with similar or identically ending reference signs. Many of the illustrated objects comprise symmetrical or complementary components that are distinguished via a supplementary letter, e.g. "L" for left and "R" for right, after the reference sign. If the statement applies to each individual component of such a symmetrical or complementary grouping, the supplementary letter is left out in some cases for the sake of clarity.

FIG. 1

FIG. 1 shows an information system 100 in accordance a first embodiment of the invention. The information system 100 is embodied in the form of an interactive spectacle system 120, i.e. interactive spectacles 120, that comprise two optical apparatuses 150. Preferably, the optical apparatuses 150 are respectively located in an inner side of a left 121L or right 121R temple of the spectacles 120. Depending on the field of application, other arrangements of the optical apparatuses 150 that do not disturb the view, e.g. in the region of a bridge 122 of the spectacles 120 that crosses the root of the nose of a user are also appropriate.

The optical apparatus 150 of the spectacles 120 is connected to a processor unit 140 via connection lines 101. If the optical apparatuses comprise photodetectors and/or light sources, the connection lines serve the transmission of electrical detection and/or control signals. The photodetectors and/or light sources can, however, be located in the processor unit 140 and be connected to the optical apparatuses 150 of the spectacles 120 via light-conducting connection lines 101. This contributes to reducing the weight of the spectacles 120.
FIG. 2

FIG. 2 shows, for the sake of understanding the invention, a detailed view of an eye 280 in cross-section. The eye 280, which is situated in two eye sockets 20 (lat. orbita) formed of skull bone in the head of a person and which is to be understood here in the sense of an eyeball 280, consists of a chamber surrounded by a translucent cornea 283 and a visibly white sclera 28. The sclera 28 is covered on its side facing the inside of the eye 280 by a choroid coat 287 that supports, also on its inner side, a light-sensitive retina 281 and supplies same with blood. Due to its pigmentation, the choroid coat 287 hinders a scattering of the light falling thereon that could disturb visual acuity.

The tissue of the retina 281 comprises two types of photoreceptor cells, i.e. rods and cones (not shown), that provide the person with the ability to see. These photoreceptor cells absorb the light focuses by an eye lens 282 in a range of wavelengths from roughly 380-760 nm and convert it, via a chain of chemical reactions, into electric nerve signals. The signals of the various nerve cells of the retina 281 are then passed on to the brain via an optic nerve 25 and processed there to a perceptible image. The numerous, highly light-receptive rods, roughly 120 million in number, are specialized for signal detection in twilight (so-called scotopic vision) and yield a grey-scale image. The roughly 6.5 million, comparatively less light-receptive cones, in comparison, are responsible for color vision during daylight (so-called photopic vision). During light absorption, an oxidation of pigments in the photoreceptor cells takes place. For the regeneration of the pigments, the cones require roughly six minutes and the rods require roughly 30 minutes. An observation period of roughly 200 milliseconds is necessary until the visual stimulus via the photoreceptors sets in and a reception of information via the retina 281 takes place.

The retina 281 comprises a depression 286 that appears somewhat more strongly pigmented due to its higher density of cones in comparison with the rest of retina. This depression 286, which is typically called the fovea centralis, lies in a region of the retina known as the macula and represents the region of keenest vision. The fovea centralis 286 is only occupied by cones, comprises a very high cone density and encompasses solely roughly 0.01% of the retina surface. The optic nerve 25 enters into the inside of the eye via a sieve-like opening in the sclera 28 in an area vis-à-vis the lens 282 designated with the reference sign 288. This area 288 does not comprise any photoreceptor cells, whence it is named "blind spot."

The chamber formed by the cornea 283 and the sclera 28 is partitioned by a deformable lens 282 and muscular ciliary processes 23 that supports the lens 282. The portion of the chamber lying the lens 282 and the retina 281, which makes up roughly two-thirds of the eyeball, forms a so-called vitreous humor 21, a gelatinous structure that consists, to over 98%, of water and that supports and protects the retina 281. The portion of the chamber lying between the cornea 283 and the lens 282 carries the name anterior chamber 22 and contains a fluid that nourishes the cornea 283. In its neutral shape, the lens 282 typically refracts the light falling on the eye such the far-away field of view is sharply imaged onto the retina 281. Through contraction/relaxation of the muscles of the ciliary processes 23, the shape and thus also the refractive characteristics of the lens 282 can be varied over a wide range in order to allow e.g. a sharp imaging of close-lying objects in the field of view onto the retina 281. In most cases, the person affected is unaware of this process.

An aperture 285 of variable diameter and consisting of colored tissue regulates the light falling onto the light-sensitive portions of the eye 280 and gives the eye 280 its characteristic coloring. Thus aperture 285 is located in the anterior chamber 22 directly in front of the lens 282 and is called the iris 285. Due to the low amount of light backscattered by the lens 282, the vitreous humor 21 and the retina 281, the central region of the iris 285 appears black and called the pupil 284. The regulation of the pupil size is also carried out by the person subconsciously.

The eye 280 is connected to the skull via six muscles 24 that run partially parallel and partially oblique to one another that allow a pivoting of the eye 280 and subsequently a change of the gaze direction. The binocular field of view captured without moving the eyes 280 encompasses roughly 170° horizontally and roughly 110° vertically. If the eyes 280 are moved, a binocular field of vision of roughly 290° horizontally and roughly 190° vertically can be captured. The region of keenest vision captured by the fovea centralis 286 encompasses solely roughly 1°. A fictitious axis through the center of this region is called the visual axis and corresponds to the direction of gaze. A rotation of the eye around the visual/optical axis is also enabled via the muscles 24.

The six muscles 24 are responsible for all movements of the eye. During observation of a fixed point, so-called microtremors of the eye 280 take place, during which the eyes 280 tremble lightly in order to avoid a temporary exhaustion of the ability of the affected photoreceptor cells to chemically react to a persistent stimulus. During a change of the direction of gaze or a movement of the head, so-called saccadic movements take place, with whose aid the fovea centralis 286 is directed to its new target of fixation or held on its previous target of fixation. During these highly complexly structured movements, the eye 280 is involuntarily moved back and forth at a small amplitude of up to several tens of degrees and with an extremely fast angular velocity of up to several hundred degrees per second. During the tracking of a moving object, the eye 280 achieves angular velocities of only one to two hundred degrees per second.

To protect the eyeball 280, people have a movable fold of skin, i.e. an upper lid 27a and a lower lid 27b that allow a closing of the eye socket 20 against external influences. The lids 27a and 27b close as a reflex in the presence of foreign objects or strong light. Moreover, the lids 27a and 27b provide, via regular, typically involuntary blinking, for an evenly distributed film of tears on the cornea 283 that washes the outer surface of the cornea 283 and protects it from drying out. The lids 27a and 27b also comprise lashes 27c that also protect the eye 280 from dust. A conjunctiva 26 covers the space between the lids 27a,27b, the eye socket 20 and the eyeball 280. The conjunctiva 26 merges, on the one hand, with the inner side of the lid and, on the other hand, with the cornea 283 and represents a second wall of protection against the penetration of germs and foreign objects.
FIG. 3

FIG. 3 shows a known embodiment of the interactive spectacles system/spectacles 320 as described above in which a signal capturing apparatus in the form of a scanning eye scanning apparatus 350D is provided. In the Figure, the left half of the Figure represents a plan view onto the head of a user 302 together with spectacles 320 having a right temple 321R, whereas the right half of the Figure reflects a cross-section of the spectacles 320 running through the left temple 321L. No further components of the information system 100 in accordance with the invention are shown in FIG. 3 other than the apparatuses belonging to the interactive spectacles 320.

In accordance with the illustrated embodiment, light beams 333a and 333b falling onto the eye 380 that originate e.g. from the field of view are sharply imaged onto the retina 381 by the lens 382 as a correlated image and are reflected back by the retina 381 as a retinal reflex image. A light beam 331 that has been reflected back in this manner passes again, in the opposite direction, through the lens 382, is focused via two concave mirrors 322 and 323 that belong to the mirror system of the spectacles 320 and is directed, as shown, onto a scanning eye scanning apparatus 350D. The eye scanning apparatus 350D comprises a signal capturing apparatus 351 in the form of a photodetector 351 that captures the light beam 331 reflected back from the retina 381 as well as two movable flat mirrors 352H and 353V that effect a horizontal/vertical deflection of the light beam 331 onto the photodetector 351. In accordance with the embodiment of FIG. 3, the spectacles 320 additionally comprises a light trap 324 that prohibits an incidence of light from undesired directions of incidence. To simplify the mirror system of the spectacles 320, this mirror 323 can be implemented via a mirrored inner surface of the spectacle lens. However, the surface must have a particular shape in order to facilitate a capturing of the entire retinal reflex image even when the eye 380 is possibly in a skewed position. This, on the other hand, limits the design freedoms of the spectacles 320.

A serial, point-by-point scanning of the retinal reflex image as a pixel sequence is carried out via the combination of a point-shaped detector 351 and corresponding control of the flat mirrors 352H and 352V. Preferably, the retina 381 is scanned with a circular, spiral or elliptical scan pattern as described in DE 196 31 414 A1 and DE 197 28 890. This has the advantage that the flat mirrors 352 can be driven without jerky movements and that a higher pixel density (number of pixels per unit of area of the retina) can be captured in the region of the fovea centralis 286.

Preferably, a suitable synchronization operation for determining the current optical axis is carried out prior to the capturing operation—to the respect that it has not already been carried out in a previous projection operation—so that the scan operation can be carried out centered to the eye.

FIG. 4

FIG. 4 shows a known embodiment of the interactive spectacles 420 as described above in which an output apparatus in the form of a scanning projection apparatus 450P is provided. In the Figure, the left half of the Figure represents a plan view onto the head of a user 402 together with spectacles 420 having a right temple 421R, whereas the right half of the Figure reflects a cross-section of the spectacles 420 running through the left temple 421L. No further components of the information system 100 in accordance with the invention are shown in FIG. 2 other than the apparatuses belonging to the interactive spectacles 420.

In accordance with the illustrated embodiment, a scanning projection apparatus 450P comprises a light source 453, e.g. a laser diode or an LED focused via a lens system, that emits a projection light beam 432 as well as two movable flat mirrors 454H and 454V. The projection light beam 432 is directed via the movable flat mirrors 454H and 454V onto a mirror system of the spectacles 420 that comprises two concave mirrors 422 and 423 that projects the projection light beam 432 onto the lens 482 of an eye 480 and, in the end, onto the retina 481. To simplify the mirror system of the spectacles 420, this mirror 423 can be implemented via a mirrored inner surface of the spectacle lens. However, the surface must have a particular shape in order to facilitate a capturing of the entire retinal reflex image even when the eye 480 is possibly in a skewed position. This, on the other hand, limits the design freedoms of the spectacles 420. To avoid the incidence of light that would be disturbing, the spectacles 420 can be equipped with a light trap 424 that hinders the incidence of from undesired direction of incidence.

A serial, point-for-point projection of an image is carried out via the combination of a point-shaped light source 553 with corresponding control of the flat mirrors 452H and 452V that respectively effect a horizontal/vertical deflection of the projection light beam 432. The projection is preferably carried out, as described in DE 196 31 414 A1 and DE 197 28 890, in a circular, spiral or elliptical scan pattern. This has the advantage that the flat mirrors 452 can be driven without jerky movements and that a higher pixel density can be projected onto the retina 481 in the region of the fovea centralis 286.

Projection

The degree of perception of an image projected into the eye 480 can be controlled in relation to the naturally perceived image via the brightness of the projected pixels. However, retinal perception is a highly complex process in which psychological effects also play a strong role. In this respect, reference is made to the relevant literature of the field.

In simplified form, however, one can say that the retina 481 adapts to the brightness of the total light falling thereon. It is known, for example, that the slight glow of the clock of a radio alarm that cannot even be perceived in daylight can appear to illuminate an entire room in a dark night. On the other hand, the strong light of headlights of approaching vehicles is barely perceptible in daylight. The brightness of a single pixel is thus perceived in relation to the pixels otherwise perceived. The retina 481 functions similarly when observed locally. If the brightness of a pixel projected onto a region of the retina 481 exceeds the brightness of the light otherwise falling onto this region by roughly 10%, then solely the projected pixel is effectively perceived by this region of the retina 481 in lieu of the other light. Due to psychological effects, the exact value can also lie between 5%-10%, 10%-15% or even 15%-20% instead of at 10%.

Preferably, a suitable synchronization operation for determining the current optical axis is carried out prior to the projection operation—to the respect that it has not already been carried out in a previous scanning operation—so that the projection operation can be carried out centered to the eye.

FIG. 5

FIG. 5A shows interactive spectacles 520 in accordance with a first preferred embodiment in which a combined signal capture and projection apparatus 550 is attached to the spectacles 520 in the region of the bridge 522. In accordance with the detailed drawing 5B, the combined signal capture and projection apparatus 550 comprises both a projection apparatus 553 as well as a signal capturing apparatus that are housed together in a protective housing 558. Light beams 530 make their way into the inside of the housing 558 and vice-versa via a translucent window 559 in an outer wall of the housing 558. The sealing of the housing 558 via the window 559, however, keeps dust, sweat and other foreign materials from disturbing operation of the combined signal capture and projection apparatus 550.

Light beams 530, 530a, 530b are captured/projected analogously to the described systems in accordance with FIGS. 3 and 4. The interactive spectacles 520 can be simplified, however, in their construction by replacing the mirrors 352/452, which are separate in the prior art, for vertical/horizontal deflection of the respective light beams 331/432 with a swivelling mirror 552/554. For the purpose of achieving a compact design, a partially transmissive mirror 556 can serve to allow separate beam paths within the housing 558 for the light 530 falling or projected through the window 559. Preferably, the inner side of the spectacle lens is provided with a surface 523 that strongly reflects beams incident from this direction that is used as a mirror for the beam path between the eye 580 and the combined signal capturing and projection apparatus 550. This contributes to a reduction of the components required and results, in the illustrated embodiment, in a simplified transmission-efficient beam path 530 in which the light beam 530 between the eye 580 and the projection/signal capturing apparatus 553/551 is only reflected three times. As described above, however, this results in a limitation of the design freedoms of the spectacles 520.

The freedom of movement necessary for a swivelling motion of the mirror 552, 554 can be achieved, for example, via a Cardan joint or spring suspension of the mirror 552, 554. Possible embodiments of such a swivelling mirror are known to the person skilled in the art, e.g. from the field of microtechnology. Further solutions to the present deflection problem in which the respective light beam 530 is deflected on the basis of electrochrome, holographic, electro-holographic or other light refraction or light reflection mechanisms are easily conceivable and equally applicable.

Although the interactive spectacles 520 are shown in a minimalist embodiment in which a combined signal capturing and projection apparatus 550 is solely provided for the left eye 580, it is self-evident that a second combined signal capturing and projection apparatus 550 having a mirror image design can be provided for the non-illustrated right eye, if necessary, in the region of the right half of the bridge 522.

FIG. 6

FIG. 6A shows a modification of the spectacles 520 illustrated in FIGS. 5A and 5B in the form of interactive spectacles 620 in accordance with a second preferred embodiment in which the left combined signal capturing and projection apparatus 550L is situated in the region lying between the left spectacle lens 624L and the left temple 621L and the right combined signal capturing and projection apparatus 650R is situated in the region lying between the right spectacle lens 624R and the left temple 621R.

Such an arrangement of the combined signal capturing and projection apparatuses 650L, 650R vis-à-vis the respective spectacle lenses 624L, 624R and the respective eyes 680 is typically associated with the necessity of either providing several mirrors along the beam path 630 (cf. mirror 322 and 323 in FIG. 3) or bestowing the respective spectacle lens 624L, 624R with a particular form in order to guarantee a capture of all regions of the retina 681. This, however, significantly limits the design freedoms of the spectacles 620. In order to circumvent this problem, the interactive spectacles 620 in accordance with FIG. 6 propose spectacle lens 624L, 624R whose inner sides are provided with a respective holographic coating 623L, 623R. Such a holographic coating 623 is capable of emulating an arbitrary reflection topology. For example, a holographically coated, flat surface can act like a spherically curved surface. Similarly, a holographically coated, spherically curved surface can act like a flat surface. The change of the effective reflection topology depends solely on the holographic content of the coating. In accordance with the Figure, the holographic coating 623L and 623R are designed and situated as mirror images to one another.

FIG. 6B contains a detailed drawing of the combined signal capturing and projection apparatus 650L. Analogously to the combined signal capturing and projection apparatus 550 illustrated in FIG. 5B, it comprises a housing 658, a projection apparatus 653 and a signal capturing apparatus 651, respective swivelling mirrors 652 and 654, a partially transmissive mirror 656 and a housing window 659.

FIG. 7

Similar to FIGS. 6A and 6B, FIG. 7A shows, in the form of a modification of the spectacles 520 shown in FIGS. 5A and 5B, interactive spectacles 720 in accordance with a third, preferred embodiment in which the left combined signal capturing and projection apparatus 750L is situated in the region lying between the left spectacle lens 724L and the left temple 721L and the right combined signal capturing and projection apparatus 750R is situated in the region lying between the right spectacle lens 724R and the left temple 721R.

FIG. 7B contains a detailed drawing of the combined signal capturing and projection apparatus 750L. Analogously to the combined signal capturing and projection apparatus 550 illustrated in FIG. 5B, it comprises a housing 758, a projection apparatus 753 and a signal capturing apparatus 751, respective swivelling mirrors 752 and 754, a partially transmissive mirror 756 and a housing window 759.

The problem of the beam path 730 touched upon above is solved in this embodiment in a space-saving manner via a special design of pads 725L and 725R. Typically, spectacles 720 are supported on the root of the nose either through the bridge 722 or through so-called pads 725. In their typically commercial design, pads are relatively flat, slightly curved and oval. Moreover, they are either hingably or swivably mounted on a projection extending from the bridge 722 in order to ensure comfortable contact of the pads to the side surfaces of the root of the nose. In the illustrated embodiment, the pads 725 are formed as fixed-shaped, elongated units that project from the spectacles 720 in the direction of eye 780 in the region of the bridge 722. On their respective longitudinal sides facing the nose, the pads 725 form the contact surfaces that support themselves on the root of the nose. In their end region lying across from the spectacles 720, the pads 725 comprise a support surface on the respective side facing the eye that is provided with a mirror or a mirroring coating, e.g. a metallic coating or a holographic coating.

Although the frame of the spectacles 720, including the pads 725, has a principally fixed form, both quasi-static, e.g. due to material fatigue and/or temperature changes, as well as dynamic deformations of the frame. Particularly when the spectacles 720 are put on and during activities in which vibrations are commonplaces, changes to the relative arrangement of the respective spectacle components to one another result. The relative location of the spectacles 720 vis-à-vis the eye 780 is also not constant. Accordingly, both the optical system of the spectacles 720, i.e. those system components that contribute to the optical signal capturing and/or the optical projection as well as any processing system connected to thereto, must be conceived and designed such that such changes in the arrangement can be taken into consideration and/or compensated and/or do not cause any extraordinary operational disturbances. This also holds for all types of interactive spectacle systems.

In accordance with the invention, the problem addressed above can be overcome in particular through a suitable signal processing of the captured signals and the signals to be generated. Furthermore, an optical marker fixed disposed on the spectacle frame in the vicinity of the typical beam path 730 can be additionally detected on a regular basis or on demand via the signal capturing apparatus 751 for the purpose of calibrating its optical system.

FIG. 8

FIG. 8 shows, in the form of a modification of the spectacles 520 illustrated in FIGS. 5A and 5B, interactive spectacles in accordance with a fourth preferred embodiment in which the signal capturing apparatus 851 of the combined signal capturing and projection apparatus 850 is capable of at least partially capturing the corneal reflex image.

The cornea is typically formed rotationally symmetric to the optical axis. Beams that fall perpendicularly onto a central region of the cornea are thus confocal to the optical system of the eye 880 and form the basis of the image truly perceived on the retina 881. Moreover, the cornea 883 consists, to a large degree, of water and exhibits, for this reason, a very high degree of reflectivity at a wavelength of roughly 1.1 µm. Since this wavelength lies in the infrared spectral region, a capturing of the corneal reflex image is primarily suitable for infrared applications, e.g. for night vision devices. Reflections occur not only on the outer, concave corneal surface, however, but also on the inside of the cornea. Moreover, due to its structure, the cornea 883 does not effect mirror-like reflections but instead effects a diffuse reflection that becomes more diffuse with increasing depth of the act of reflection within the cornea.

In order to obtain a meaningful corneal reflex image, effectively only those beams that fall perpendicularly onto a central region of the cornea are captured in the illustrated embodiment. This is achieved through several measures. Firstly, the spectacle lens 824 situated in front of the eye whose side facing the eye 880 is provided with a surface 823 that is high reflective for beams incident from this direction comprises a specially designed shape that focuses the light perpendicularly reflected from the cornea such that it falls onto the signal capturing apparatus 851 as light beams 834 that run nearly in parallel whereas light that is reflected non-perpendicularly from the cornea is deflected in another direction. Alternatively, the spectacle lens 824 can be designed in another fashion, yet comprise a partially transmissive, holographically reflecting layer 823 that likewise effects such a focussing of the light reflected perpendicularly from the cornea such that it falls onto the signal capturing apparatus 851 as light beams 834 that run nearly in parallel, whereas light non-perpendicularly reflected by the cornea is deflected in another direction. Secondly, an aperture 857 is provided shortly in front of the signal capturing apparatus 851 that prohibits a capturing of those light beams whose incident angle lies outside a narrow range of incident angles of the light beams 834 that run nearly in parallel as described above.

FIG. 9

FIG. 9 shows, in the form of a modification of the spectacles 520 illustrated in FIGS. 5A and 5B, interactive spectacles in accordance with a fifth preferred embodiment in which a spherical or spherical-acting, partially transmissive, mirroring supplementary element 929 is arranged between the spectacle lens 924 and the eye 980. Preferably, the supplementary element 929 is arranged confocal to the optical system of the eye 980.

The degree of reflectivity of such a supplementary element 929 can be adapted to the requirements of the information system. One can choose between a high degree of reflectivity, which allows very good capturing of light beams 933a-933c directed onto the eye 980, and a low degree of reflectivity, which avoids impairment of the perception carried out by the eye 980. Preferably, the supplementary element 929 exhibits a low (e.g. less than 10%), homogenous degree of reflectivity over its entire reflective surface. On the other hand, reflecting organs of the eye 980, for instance the cornea 983 or the retina 981, exhibit, in part, very strong local reflective dependencies. Similar statements hold for the spectral reflective dependencies of the supplementary element and/or the reflecting organs of the eye 980. Whereas the supplementary element 929 can be preferably designed such that it exhibits a homogeneous degree of reflectivity over all relevant spectral ranges, the various organs of the eye 980 exhibit highly differing degrees of absorption that, in many cases, are also subject to strong local variations.

Excepting partial reflection, the supplementary element 929 should have as little effect as possible on the light falling thereon. For this reason, the supplementary element 929 is preferably manufactured of a homogenous, translucent and uncolored material and is manufactured to have a constant thickness in the direction of the light beams directed toward the center of the eye. By applying an anti-reflective coating to the side of the supplementary element 929 facing the eye 980, improved translucency can be achieved.

The reflecting contour of such a supplementary element 929 is well defined and can thus be supplied to the information system as known information, whereas the contour of the relevant reflecting organs of the eye 980 must first be determined. In some respects, latter encompasses significant difficulties. The capturing of the light beams 933a-933c directed onto the eye 980 can thus yield valuable images of the field of vision.

In the illustrated embodiment, effectively only those beams that fall perpendicularly onto the supplementary element 929 are captured. This is achieved through the following measures:

Due to the partially reflective surface of the supplementary element 929, a corresponding portion of those beams 933a-933c that fall perpendicularly onto the surface of the supplementary element 929 are reflected back perpendicularly, whereas other beams are reflected back from the surface of the supplementary element 929 correspondingly skewed in accordance with the law of reflection "The angle of incidence equals the angle of reflection." The light beams reflected back perpendicular to the surface of the supplementary element 929 travel back the same way they came and are thus incident upon the spectacle lens 924 situated in front of the eye. The side of the spectacle lens 924 facing the eye 980 is provided with a surface 923 that is highly reflective for beams incident from this direction and comprises a specially designed shape or a specially formed coating that focuses the light beams reflected perpendicularly by the supplementary element such that they fall onto the signal capturing apparatus 951 as light beams 934 that run nearly in parallel whereas light beams reflected non-perpendicularly by the supplementary element are deflected in another direction. In addition, an aperture 957 is provided shortly in front of the signal capturing apparatus 951 that prohibits a capturing of those light beams whose incident angle lies outside a narrow range of incident angles of the light beams 934 that run nearly in parallel as described above.

If the image of the field of view captured via the supplementary element 929 is to be the basis for a projection correlated with the actually perceived field of view, then the correlation between the captured light and the perceived field of view must be determined. In accordance with the illustrated, fifth embodiment, this correlation is achieved through a preferably confocal arrangement of the supplementary element 929 to the optical system of the eye 980. It is thus preferred that the supplementary element 929 be fastened to the spectacles via an adjustable suspension such that the position of the supplementary element 929 can be adjusted in both vertical as well as two horizontal directions.

Confocality is principally given when the supplementary element 929, in terms of optics, is situated rotationally symmetric to the optical axis and is spaced from the lens 982 such that the optical mid-point of the optical system of the eye agrees with the mid-point of the sphere defined by the spherical or spherical-acting supplementary element. The optical axis can be sufficiently determined for this purpose via the orientation of the pupil 984 that is easily recognizable via its sharp contours and whose orientation is easily determinable due to its round shape. In addition, due to the spherical or spherical-acting shape of the supplementary element 929, no pivoting of the supplementary element 929 around the possible pivotal axes of the eye 980 is necessary to ensure confocality since, even the case of a skewing of the eye, at least a substantial portion of the supplementary element 929 remains, in terms of optics, rotationally symmetric to the optical axis through a corresponding vertical and/or horizontal shift of the supplementary element 929. As regards the distance to the lens 982, there are various possibilities for determining the necessary distance. For example, an optical or acoustic measurement of the cornea 983 can be carried out whose curvature yields a very good estimate of the correct location of the supplementary element 929. Retinal or cornea reflex images can also be at least partially captured, and the correct distance can be determined on the basis of a comparison of the reflex images with the light captured via the supplementary element 929.

Due to the spherical or spherical-acting implementation, e.g. through a holographic coating, of the partially reflecting surface of the supplementary element 929 as well as through this confocal arrangement of the supplementary element to the eye 980, solely those beams 933a-933c that fall perpendicularly onto the surface of the supplementary element 929 are confocal to the optical system of the eye 980 and thus correspond to the beams falling onto the retina.

FIG. 10

FIG. 10 shows a plan view (FIG. 10A) and a front view (FIG. 10B) of spectacles 1020 in accordance with a sixth embodiment in which two sensor apparatuses 1061R and 1061L, e.g. two solid-state cameras, for instance CCD or TTL cameras, are provided for the purpose of further signal capturing, in particular from the visible field of vision. FIG. 10B also shows the left and right eye 1080L,1080R of a possible wearer 1002 of the spectacles 1020. For the sake of clarity, however, no other features of the user 1002 are represented in FIG. 10B.

To avoid the occur of parallax between the images captured by the respective camera 1061R, 1061L and the images received by the eye associated therewith, the cameras 1061 should be arranged as coaxially as possible to the eyes with regard to their "optical axes." In view of the system size of such solid-state cameras 1061 and the current state of the art, it has turned out to be meaningful to located the cameras 1061 in the front region of the respective temples 1021L, 1021R as shown. A mounting in the region of the bridge 1022, e.g. in the pads 1025, is also meaningful. After a further miniaturization, the solid-state cameras 1061 will be able to be located in the spectacle frame over the respective spectacle lenses 1024L, 1024R in order to achieve further axial identity. It is foreseeable that solid-state and other types of light capturing systems will, in the future, be able to be built into the spectacle lens 1024, which can naturally be glass, plastic or other translucent material. Such an arrangement of the cameras 1061 would allow a signal capturing that is coaxial and nearly confocal with the eye 1080L, 1080R.

In a non-coaxial arrangement of the sensor apparatus 1061 to the respective eyes 1080L, 1080R, the information obtained from the sensor apparatuses 1061 should be brought into correlation with the eyes 1080, as need be. Such correlation is particularly important when the sensor apparatuses 1061 are implemented by cameras 1061 and a superimposed image based on image information obtained from the cameras 1061 is to be projected into the respective eye 1080L, 1080R.

If the image captured by the cameras 1061 is simply projected on the respective eye 1080L, 1080R, so-called parallax occurs, in which the "field of view" of the respective camera 1061L, 1061R does not agree with the naturally perceived field of view. In particular during a skewing of the eye 1080 deviating from the neutral position, or in the case of objects lying closer in the field of view, parallax would lead to abnormal perception in the case of superimposition since, in such cases, the optical axis of the eye 1080 would lie skewed to the "optical axis" of the respective camera 1061L, 1061R.

During correlation in this sense, only the portion of the image captured by the cameras 1061 is projected into the respective eye 1080L, 1080R that lies in corresponding "correlation" to the optical axis of the respective eye 1080L, 1080R. In the simplest case, an at least partial reflex image of the field of view is captured from the respective 1080L, 1080R via the signal capturing apparatus 1051. Characteristic pixels that can be found in both the captured reflex image as well as in the images captured by the cameras 1061 then serve as reference points for a perspectively correct projection of the image information captured by the cameras 1061 onto the eye 1080. Similarly, the signals captured from the eye 1080 can serve to determine the gaze direction of the respective eye 1080L, 1080R with respect to the coordinate system of the spectacles 1020 in order to carry out a mathematically based correlation from this angular information.

t a correlation is also meaningful in the context of system applications in which the eyes 1080 are hindered from perceiving the field of view. This is the case, for example, during use of occluded, so-called "virtual reality" glasses 1020 (as shown, yet with non-translucent lenses 1024) wherein solely a synthetically generated image is presented to the eyes 1080. In such a case, the aforementioned correlation can consist, for example, of capturing the gaze direction of the eye 1080 as described above and projecting a virtually generated image that corresponds to the orientation of the respective eye 1080L, 1080R. In this case, however, the spectacles 1020 serve as a coordinate system. If, however, the position and orientation of the spectacles 1020 is also determined, e.g. on the basis of the images captured by the cameras 1061, then a correlation between the respective eye 1080L, 1080R and the surroundings can be created. Such a system could be used, for example, in a virtual amusement house, similar to a house of horrors. Someone who's currently standing on a conveyor belt could have, for example, a virtual image projected into the eyes that gives him the feeling he is running on floating tree trunks in the middle of a wild river.

At this point, it should be underlined that the information system described above on the basis of FIGS. 5 to 10 must not necessarily operate with a combined signal capturing and projection apparatus. It is equally possible to work with an embodiment of the system in which the signal capturing apparatus is separate from the projection apparatus and/or in which one of the two apparatuses is missing.

FIG. 11

In accordance with a seventh embodiment, the information system in accordance with the invention comprises means that allow the provision of a telescope function. FIGS. 11A and 11B illustrate the perceivable effect of the telescope function to a user. FIG. 11A shows the naturally perceived field of view 1190 of a user of an information system designed in accordance with the seventh embodiment. Although the field of view 1190 encompasses roughly 170° of the surroundings horizontally and roughly 110° of the surroundings vertically, solely a small region 1191 of several degrees around the visual axis forms the region of keenest sight 1191.

Via its capturing of light from the field of view and the aforementioned possibility of a projection of image information into the eye, the information system can be designed such that this region 1191 is projected, optically enlarged, onto the region of keenest sight 1191 after corresponding processing of the captured pixels via an evaluation apparatus comprised by the information apparatus, e.g. upon pressing of a button. As described above, the degree of perception of an image projected in this manner in relation to the naturally perceived image can be controlled via the brightness of the projected pixels. If the field-of-view light is captured, for instance, as a reflex image from the eye, a spatial or temporal separation of the capturing and the projection will ensure that the projection does not influence the capturing.

In the case of a conventional telescope, the spatial relationship to the surroundings is lost on account of the fact that the entire field of view is shown in enlargement. As a consequence, a person looking through a telescope cannot walk or drive at the same time. This phenomena is well known.

Since the information system in accordance with the invention can determine, via its capturing of signals from the eye, the visual axis/the position of the fovea centralis relative to the optical system of the spectacles, the information system is capable of avoiding this disadvantage of a conventional telescope. For example, the projection can be carried out in a manner as shown in FIG. 11B in which solely a small region 1191 lying directly around the visual axis in the natural field of view is projected onto the fovea centralis in enlargement, whereas no projected image information is superimposed on the remainder of the field of view. The scene peripherally perceived by the user thus stays the same in spite of telescopic presentation of the most relevant region of the field of view. In order to achieve this effect, the brightness of the image information projected into the eye must naturally be chosen such that the desired relationship of perception between the natural and the projected image results. This system also has the advantage that the amount of image processing necessary for the enlargement is held within limits since only a selected image region 1191 of the field of view 1190 is processed.

In accordance with an elegant embodiment not shown, an enlarged image is projected into the eye such that the projected image in an annular border region between the region of keenest sight 1191 and the remaining region of the retina is enlarged more strongly as it gets closer to the visual axis. In this case, no enlargement takes place along the outer edge and along the inner edge an enlargement takes place with the same "zoom factor" as the enlarged image projected into the inside of the ring, i.e. onto the fovea centralis. Thus, when the brightness of the projected image information is correspondingly chosen, a soft transition between the peripheral scene and that which is telescopically seen results.

FIGS. 11C and 11D schematically illustrate how an enlargement of the image naturally falling onto the fovea centralis can be achieved through a modification of a scan pattern 1138, 1139 during the scanning of a reflex image. Although projection pattern 1137 and scan pattern 1138, 1139 are illustrated in the same plane in FIGS. 11C and 11D for the sake of explanation, it could be, in the information system in accordance with the invention, that projection takes place onto the retina, whereas the scanning takes place, for example, from the cornea.

FIG. 11C schematically illustrates a typical scan pattern 1138 that scans the region 1189 of the cornea or retina reflecting the field of view. In this vastly simplified example, it is assumed, for the sake of comprehensibility, that the respective pixels of the sequentially scanned image are projected back, after image-processing preparation if need be, in their proper sequence as corresponding images of the sequential image projected into the eye. In the illustrated example, the scan pattern 1138 thus corresponds to the projection pattern 1137 in spite of possible spatial or temporal separation of the scan beam and the projection beam. If an enlargement of a central region of the field of view is desired, then the scanning can be effected in accordance with a modified scan pattern 1139 that effects an increase in the density of the captured pixels in that central region. If these pixels captured at higher density are projected back correspondingly, yet at lower density during the projection, then an enlarged image is the result.

FIG. 12

In accordance with an eighth embodiment, the information system in accordance with the invention represents a guidance system. For this purpose, the information apparatus of the information system comprises position sensor e.g. acceleration measurement apparatuses or GPS receivers as well as a data bank or data bank connection that supplies orientation data. Such a data bank can be implemented e.g. via a CD-ROM carrying the data, a DVD or another exchangeable storage medium in connection with a corresponding reading device. Methods and apparatuses for obtaining position fixing information that, for example, determine the current location or allow their determination via a combination of such orientation data with data obtained from the position sensors are known. In a typical apparatus, the orientation data comprise map information that are used for position determination in conjunction with signals supplied by the position sensors. The establishment of a correlation or a dependency, e.g. when such position information is obtained or presented, between the signals captured from the eye or light captured from the field of view and the provision of information, however, far exceeds that known to the art.

FIGS. 12A to 12E show the field of view 1290 perceived by a user of an information system designed in accordance with an eighth embodiment. In such an information/guidance system, the captured field-of-view light is evaluated with respect to the positioning information obtained via a pattern recognition that takes the data available for the determined whereabouts into consideration. Orientation hints such as characteristic buildings, side streets, or the like that are to be expected for the determined whereabouts are thereby recognized such that e.g. visual or acoustic guidance/identification can be carried out, if necessary.

In the illustrated example in accordance with FIG. 12A, the guidance system serves for navigation. In this case, it is determined, e.g. based on a computed or predetermined route, available map information and the current whereabouts, that one should turn into the second street on the right side. This street is recognized on the basis of the captured field-of-view light via pattern recognition, in response to which a hinting arrow pointing at the street is locationally correctly blended into the field of view via projection taking into consideration the gaze direction determined by the system. Similarly, the guidance system could provide the driver with an acoustic message, e.g. "turn right after 50 meters" or "now turn right."

In the example illustrated in FIGS. 12B and 12C, the guidance system serves to provide information. For example, a user can selectively be provided information about his direct surroundings. In accordance with FIG. 12B, a tourist using the information system looks at a characteristic building and actuates an activation button that is physically present or virtually blended into the field of view. The building is subsequently identified on the basis of the determined whereabouts and a pattern recognition based on the captured field-of-view light or an electronic compass that determines the direction of the head. In response, information about the building is provided. This information can originate from a data bank or other information source and can be selected, e.g. interactively, via context-dependent menu that visually or acoustically lists the information available for selection for that particular building. The selection can be carried out via voice control or via fixation with the eyes. Further information re eye-controlled menu selection will be described in a later section of this description.

In accordance with FIG. 12B, historic data are blended into the field of view via projection. In doing so, the system determines, from the captured field-of-view light, a suitable blend-in position, e.g. in front of a monotonous roof or in front of the sky. The data are blended in in accordance with the blend-in position. Typically, the fovea centralis is not directed at the blend-in position at first, whence the blended-in data is first perceived as an unfocussed, peripheral appearance. The locationally fixed, blended-in data are not imaged upon the fovea centralis until a corresponding pivoting of the gaze direction in accordance with FIG. 12C. If the gaze is directed at another building recognized by the system, then the blend-in information can change in accordance with FIGS. 12D and 12E. In the Figures, the circle 1290 represents the perceived field of view, whereas the circle 1291 designates the region of the field of view captured by the fovea centralis.

Through a compact and portable design as shown in FIG. 1, such an orientation system could be worn by a pedestrian, a bicyclist, a motorcyclist or other vehicle driver.

FIG. 13

In accordance with a ninth embodiment illustrated in FIGS. 13A and 13B, the information system in accordance with the invention acts as a driving aid. The Figures show the perceived field of view 1390 of a user of such a system.

Preferably, the information apparatus of the information system comprises a distance sensor, e.g. an optical or acoustic distance measuring device or a radar apparatus, or is connected to a corresponding distance measuring system that determines the distance between a vehicle and objects located in front of the vehicle in the direction of motion. In the case of a stereoscopic capturing of light from the field of view, the distance could be determined via a computation of parallax in which change of position of the object in a respectively captured left and right image conveys information re the distance.

If, for example, it is determined, via an evaluation apparatus also comprised by the information apparatus, that the vehicle is on a collision course with the object, then e.g. a warning symbol 1395 can be blended in in the region of keenest sight 1391 and a warning circle 1394 can be blended in around the dangerous object by means of projection as described above. If the object is located outside or on the edge of the region of peripheral vision, then a further warning symbol 1395*a* can attention to where the danger lurks. This is illustrated in FIG. 13A.

Other information relevant to driving safety can also be determined via sensors or the captured field-of-view light. For example, an evaluation apparatus could recognize the road lane markings of a road lane lying within the field of view via pattern recognition and compute the highest allowable speed, in particular in curves, therefrom. If the information system determines, independently or via connection to the instrument system of a vehicle, that the vehicle has exceeded this computed highest speed, then a warning symbol 1395 can be blended in in the region of keenest vision 1391. This is illustrated in FIG. 13B. The advantage of blending in of a warning symbol 1395 in the region of keenest vision 1391 lies in the fact that the symbol 1395 appears where the eye is looking and thus does not tempt the eye to look away from the present scene. For this reason, the brightness of blended in symbols should be chosen such that the symbol appears translucent. Attention can also be drawn to the danger acoustically.

FIG. 14

FIGS. 14A and 14B show an information system in accordance with the invention in accordance with a tenth embodiment that exemplifies the possibilities of a complex, multifaceted information system. In the concretely illustrated example, the illustrated information system comprises a mobile fire department command center 1410 that comprises a command console 1412 as well as several helmet systems 1411.

Each of the helmet systems 1411 comprises a signal capturing apparatus as described above as well as a field-of-view capturing apparatus. Each of the helmet systems 1411 can optionally be equipped with a projection apparatus, infrared sensors and/or position sensors. They can also be equipped with further sensors that allow e.g. an assessment of the air quality. For the purpose of communication, each of the helmets 1411 is equipped, for example, with a radio transmission system that communicates with the command center 1410 and/or the command console 1412 and that takes over both tasks of an information apparatus as well as tasks of an output apparatus via its transmission and reception of information.

Preferably, the field-of-view images captured by the respective helmets 1411 which can be brought into agreement with the truly perceived field of view of the respective firemen on the basis of the signals captured from the eyes are transferred to the command console 1412 and presented there on monitors. In order to reduce the amount of data to be transmitted, users of the command console 1412 can also wear a projecting spectacle system so that solely the image data falling onto the region of the user's fovea centralis must be captured and/or transmitted in high resolution. A correlated field-of-view image of an individual fireman or a mosaic of several images could be projected into the user's eye. Thus, the user could see exactly that which the fireman sees or be provided an image from the fireman's field of vision that changes depending on his own eye movements.

In the optional case of a projection, additional information could be woven into the image projected to the user and/or the fireman. For example, orientation and/or temperature information obtained via the position sensors and/or infrared sensors could be blended into the field of view. Constantly blending in particular points on a compass such as North and West as well as altitude information could be helpful reference information both to the user far away from the action he is seeing as well as to the fireman veiled in smoke and haze.

Through appropriate pre-processing of the captured position information and due to the inherent networking of the system components, the position of his colleagues, e.g. via a characterizing "X," or the position and severity of the sighted or otherwise captured hearts of the fire, e.g. via a dot that is colored in accordance with the strength of the fire, could be blended in to each fireman. This would make fighting the fire easier and would reduce the probability of accidentally injuring a colleague hidden behind smoke or a wall.

FIG. 15

FIG. 15 shows an information system in accordance with the invention in accordance with a eleventh embodiment in which the information system serves the operation of an external system, e.g. a remote controlled robot 1579 designed to move dangerous objects.

In accordance with the illustration, the robot 1570 movable on wheels comprises a camera apparatus 1571 as well as a grasp arm 1572. The robot 1570 is connected to a spectacle system 1520 worn by a user 1502 e.g. via a radio connection. The images captured mono- or stereoscopically via the camera apparatus 1571 can be mono/stereoscopically projected onto the retina of the user 1502 via a projection apparatus comprised by the spectacle system 1520. In the case of a stereoscopic projection, spatial vision would be ensured.

If the camera apparatus 1571 is provided with a macroscopic lens having a wider "field of view" than the field of view of the user 1502, then the field of view seen by the user 1502 can be held in correlation with the remote image as a function of the captured eye movements of the user 1502 via a corresponding selection of an image detail from the image supplied by the camera apparatus 1571 as described above. The movements of the head of the user 1502 can also be captured via position sensors such that the camera apparatus 1571 pivots in correlation with the head movements. The information system in accordance with the invention thus offers a previously unachieved degree of visual authenticity during the perception of a remote scene, which considerably eases the control of such an external system 1570.

Attaching a microphone to the external system, in particular a directional microphone that is directed as a function of the head position or the gaze direction, in connection with the headphone arrangement on the spectacle system allows a further sensory dimension to be realized.

In order to allow further operational control of the robot 1570, a manually operable joystick 1525 is connected to the spectacle system 1520 e.g. via a cable 1526. Thus would allow, for instance, the grasp arm 1572 or the direction of motion of the robot 1570 to be controlled in several directions.

FIG. 16

FIG. 16 schematically illustrates an information system in accordance with the invention in accordance a twelfth embodiment in which a spectacle system 1620 acts as a universal remote control for one or more devices, for instance a computer, a video recorder 1676, a printer 1677, a slide projector and/or a telephone 1679.

In the illustrated system, the spectacle system 1620 provides an interface that communicates in two directions between a user 1602 and the device 1675-1679 to be controlled. First, the device 1675-1679 must be recognized. This is fundamentally carried out, consistent with the invention, by gazing at the device 1675-1679 to be operated with the fovea centralis. The identity of the gazed-at device 1675-1679 can be determined either with or without the assistance of the device 1675-1679. In the following, it is assumed that both the device 1675-1679 as well as the spectacles 1620 are equipped with the signal reception and/or transmission apparatus necessary for the operations described. If the identity is determined with the aid of the device 1675-1679, then this device 1675-1679 either radiates an ID-signal e.g. an infrared or ultrasonic signal, in more or less regular intervals or it is requested by a request signal radiated by the spectacles 1620 to radiate an ID-signal. The request signal must be radiated localized to the gaze direction in order to avoid addressing other devices. The ID-signal radiated by the device 1675-1679 is recognized by the spectacles, as a result of which conclusions are made re the identity of the device.

If the identity is determined without the aid of the device 1675-1697, then the spectacles 1620 carry out a pattern recognition of the gazed-at region of the field of view in cooperation with a databank or other information source 1640 that contains pattern recognition data for the respectively addressable devices 1675-1679.

Based on the identity of the device 1675-1679, a menu that is adapted to the possible functions of the device is blended in, at a fixed location, into the field of view of the user 1602, if necessary upon the pressing of a button or the blinking of an eye. If the functionality of the spectacles is not readily known, then the corresponding information is first established from a databank or other information source 1640, e.g. via standardized interrogation of the device itself. In this case, identification of the device embedded into the interrogation signal ensures that solely the desired device responds to the interrogation. By blending in the menu into the field of view at a fixed location, the user 1602 can control the menu, which may be hierarchical if necessary, via slight eye movements like a computer menu.

After the desired function has been selected, a signal corresponding to the function is sent from the spectacles 1620 to the device 1675-1679. In this case, identification of the device embedded into the signal can ensure that solely the desired device reacts to the signal.

In this manner, quick and easy operation of many devices can be achieved with little hardware.

FIG. 17

FIG. 17 shows an optical system in accordance with a thirteenth embodiment in which a hinged mirror 1755 allows a switching between a capturing from the field of view and a capturing from the eye 1780 or a projection onto the retina 1781.

The advantage of this optical system lies in that the same swivelling mirrors 1754H and 1754V can be used for a capturing from the field of view and for a projection onto the retina 1781 and that the beam path for a capturing from the field of view and the beam path for a capturing from the eye 1780/a projection onto the retina 1781 is, to a large degree, accordingly identical. In this manner, a high correlation between the light captured from the field of view and the signals captured from the eye/a high correlation between the light captured from the field of view and the image projected onto the retina is achieved through the optical system itself. This means that no additional correlation errors are caused by the aforementioned beam paths travelling across different swivelling mirrors that could exhibit different rotation characteristics. For capturing light from the field of view and capturing light from the eye, even the same light capturing apparatus 1751 can be used. The correlation can solely be negatively influenced by the reflection on the spectacle lens 1724 and the optical system of the eye 1780.

Non-Illustrated Embodiments

Further to the embodiments illustrated in the Figures, further possible embodiments of the information system in accordance with the invention will be described hereinafter for the sake of a better understanding of the invention.

TV Newspaper

Previous electronic books and/or newspapers have the disadvantage of being too heavy and/or too unwieldy and can moreover only present a limited amount of information per page. Portable video and TV devices are also heavy and/or unwieldy. If the information system in accordance with the invention is designed such that the provision of information comprises a projection of image information into the eye, then various vision-related media, e.g. electronic books or newspapers, television or video games, can be implemented via the information system. In such case, the information system in accordance with the invention is implemented, for example, in the form of wearable spectacles as described above that can be connected e.g. to an information network, a portable storage apparatus, e.g. a CD-ROM or DVD-reading device or another information source via a cable, infrared or radio connection.

An advantage of such a design of the information system in accordance with the invention is that its capturing of signals from the eye in conjunction with a field-of-view capturing allows a projection in which the projected text and/or the projected images appear to be fixed in space. For this purpose, the information apparatus comprises an evaluation apparatus that determines the correlation of the visual axis to the field of vision and that accordingly controls the projection such that the information projected onto the eye appears to be immovable vis-à-vis the field of vision in spite of movements of the eye. The determining of the correlation of the visual axis to the surroundings can also be assisted by position sensors mounted in the spectacles.

The virtual position of the fixation fixed e.g. via a fixation with the eye in conjunction with a blinking of the eyes or a pressing of a button or even automatically, for example by means of an image-processing evaluation of the field of vision that determines an area of the field of vision having as little content as possible. The disruptive effect of the natural field of view not necessarily covered up by the projection of information can be reduced via a complementary-color "wiping out" in which complementary-colored pixels are determined on the basis of the light captured from the field of view whose correlated projection onto the respectively associated regions of the retina make the natural background appear white on account of the addition of colors. If a black background is desired, then the perceived total brightness of the projection must exceed the perceived total brightness of the natural field of view by roughly 10% to 20% as described above so that even the brightest points of the natural field of view are perceived as black.

For the sake of controlling operation, image information representing virtual control knobs can be projected into the eye such that they likewise appear fixed in the vicinity of the text and/or image in the field of view. The virtual information medium could thus be remote controlled, i.e. page turning, fast forwarding, rewinding or the like, by gazing at the corresponding control knob with the fovea centralis plus pressing a button or blinking an eye. Similarly, access to lexica, databanks, etc. could be made possible by gazing at presented words or image sections. Instead of control knobs, the information system could also be controlled, for example, via menu guidance in which control menus "pop-up" when a particular region of the image is observed in order to allow an ocularly controlled selection from the menu which may be hierarchically constructed, if necessary.

A further advantage of such a design of the information system in accordance with the invention is that the amount of data necessary for a sufficient, momentary presentation is far less than the amount of data that would be necessary for a high-resolution presentation of the entire field of view. This is due to the fact that the information system has knowledge of the region of keenest sight. Thus, only those portions of the projection must be carried out at high resolution that regard the region of the fovea centralis. Onto the other regions of the retina, a projection having a lower pixel density suffices. The amount of data necessary for an instantaneous presentation is accordingly reduced, which has clear system advantages. In particular, the perceived size of the projected image may be arbitrarily chosen without unprocessably large amounts of data for presentation of the instantaneous image being the result.

If the projected image is larger than the field of view, then the current visual axis determines the cropping of the image. The projection is carried out such that the current image detail fills the entire active region of the retina. By moving the eyes, further sections of the image can be brought into the field of view. If the projected image is smaller than the field of view, then projection must only be carried out onto a limited portion of the retina. If the natural background of the field of view is not blended out, then this changes during movements of the eyes. In particular for television or cinema-like presentations of information, a projection that fills the field of view exactly is preferred.

If signals are captured from both eyes of a user, then the projection can be carried out stereoscopically, wherein a slightly different image is supplied to each eye such that the brain believes to perceives a three dimensional total image. This allows an optimal system-human interface e.g. for 3D television, 3D video games, 3D CAD applications or other, in particular interactive, 3D applications to be realized. Preferably, the information system comprises further control elements, for example a joy stick, pedal or steering wheel that allows a navigation and/or change of perspective within the presented virtual image or other influencing of the presentation of information or of a system connected with the information system. As described above, the eye itself can also act as a control element.

By accordingly applying the above measures necessary for the positioning of an electronic newspaper at a virtual location, it is likewise possible to project the person wearing the information system in accordance with the invention other orientation aids onto the retina such as, for example, an artificial horizon.

Ophthalmological Applications/Visual Aids

Due to its capturing of signals reflected back from the eye, the information system in accordance with the invention is excellently suited for embodiment as an ophthalmological system. For example, the information system in accordance with the invention can be implemented as a positioning system for ophthalmological surgery, in particular for ophthalmological laser surgery. The information system in accordance with the invention can also be used e.g. as an ophthalmological diagnostic system, visual aid system and/or visual deficiency correction system.

Most of the structures or organs of the eye are very small in comparison to manual movements. Diseases and injuries to these structures/organs often only affect a small, microscopic area. As opposed to many other parts of the body, the eyes, however, cannot be fixed, which makes the treatment of possible diseases or injuries to the eye particularly difficult.

Due to the ability of the information system in accordance with the invention to exact follow movements of the eye and provide information with regard to the momentary position of the eye even to other systems, these difficulties can be overcome via a therapeutic system on the basis of the information system in accordance with the invention. For example, the therapy system can be connected to the information system in accordance with the invention for the purpose of exchanging information in such a manner that the information with regard to the momentary position of the eye is provided to the therapy system such that a high-precision, automated therapy of the eye can be carried out even when the eye is moving.

In accordance with another embodiment, a therapeutic laser beam is directed via the optical system of the information system in accordance with the invention. A laser treatment of the eye, in particular of the retina, can thus be carried out in the same manner as a projection as described above. For example, diseased veins in the choroid coat can be stultified in that a photosensitive preparation is injected or taken in and that the diseased portions of the choroid coat are precisely irradiated for several tens of seconds. Such a therapy can be precisely carried out with the aid of the information system in accordance with the invention.

In order to be used as a visual aid and/or visual deficiency correction system, the output apparatus of the information system comprises a projection apparatus that projects the vision-improving image information onto the retina. In addition, the information apparatus comprises an evaluation apparatus that determines the vision-improving image information on the basis of the light captured from the field of view. The vision-improving image information is preferably projected onto the retina in correlation with the signals captured from the eye such that the naturally perceived field of view and the projected image information are perceived as a unitary image. In extreme cases, the vision-improving image information is projected onto the retina such that the otherwise naturally perceived field of view is not at all perceived by the eye. As described above, the degree of perception of an image projected in this manner in relation to the naturally perceived image can be controlled via the brightness of the projected pixels.

Such an information system allows e.g. vision deficiency correction for short or far-sightedness as well as for color blindness to be carried out. During the correction of short or far-sightedness, the information system can set to a (quasi-) fixed correction, can allow a variable correction, or can automatically, dynamically adjust itself to the visual deficiency. The correction is carried out via an adjustable (if need be), optical focussing system within the projection apparatus or via image processing measures. Latter can be implemented at low system cost.

Implementations with (quasi-)fixed or variable correction are understandable to the person skilled in the art without further explanation due to inherent similarity to similar optical systems. An implementation with a dynamic, automatic correction of the natural imaging error comprises, in addition to the aforementioned correlation, a further dependency on the signals captured from the eye. In such case, in particular a retinal reflex image is captured that supplies, via comparison with light captured from the field of view and/or via image processing evaluation, information re the sharpness of the image imaged onto the retina. The light captured from the field of view is accordingly processed into vision-improving image information and projected onto the retina. The information system can also act as a diagnostic system through output of the correction values determined in this manner.

Due to its capturing of signals reflected back from the eye and light originating from the field of view, the information system in accordance with the invention is in a position, by means of a correspondingly programmed evaluation apparatus, to supply information about many ophthalmologically relevant characteristics of the eye. For example, squint angle, primary positions (PP), visual field testing even with colors, threshold tests, standardized testing methods for glaucoma diagnosis, retinal function tests (e.g. ERG and VEP) even at selected locations and tests of the receptive fields can be carried out/determined. The person skilled in the art selects the signals to be captured from the eye for this purpose, the field-of-view stimuli necessary for this purpose and the processing algorithms necessary for this purpose on the basis of his specialized knowledge, accordingly taking into consideration the invention described above.

Whereas e.g. the keenness of the vision can be determined through an evaluation of signals reflected back from the eye and can be subsequently corrected, the correction of many other visual deficiencies presumes a system-independent determination of the deficiency, for example by an ophthalmologist. A befitting setting of the correction carried out by the information system can be carried recursively or simply.

In a recursive adjustment process, a correction is carried out by the information system in accordance with a previous setting while the visual acuity of the person with defective vision is being tested. On the basis of the results of the tests, a new setting of the information system is chosen. This process is repeatedly carried out until the visual deficiency has been sufficiently compensated. In this manner, the information system acts equally as a diagnostic system since the visual deficiency can be determined based on the best-correcting final setting.

In a simple setting processing, the visual acuity of the person with defective vision is tested without any type of compensation. Based on the results of the tests, a suitable setting of the information system is chosen that then, in later operation, prepares the light captured from the field of view into vision-improving image information in accordance with this setting and projects it onto the retina. During the preparation, e.g. particular spectral components or particular regions of the field of view are emphasized or modified through other image processing measures in accordance with the setting, i.e. the original visual deficiency.

For people suffering from night blindness, a visual aid can be realized via the information system in accordance with the invention, for example, in that the light captured from the field of view, e.g. via highly light-sensitive photo-detectors, is strongly amplified and projected onto the retina. In this manner, the cones can be stimulated in such manner that predominantly color, photopic vision instead of scotopic vision takes place. Also, the maximally allowable brightness of the individually projected pixels is limited to a predetermined threshold value in order to avoid a glaring through brightly illuminating objects such as street lamps and oncoming cars. Such a system is thus also suitable as an anti-glare system since, if the brightness of the entire field of view is raised, whereas the "excessive" brightness of individual pixels is left unchanged, then the "excessively" bright pixels are not perceived as being "excessively" bright. If the information apparatus also comprises an infrared sensor that captures infrared light from the field of view, then additional, monochrome image information with regard to the field of view can be obtained by night or fog that can be transformed into the visible spectral range in order to improve the image information already obtained via the field-of-view capturing apparatus and the evaluation apparatus.

In general, the information system in accordance with the invention can also be suitable for improving visual acuity. E.g. in the case of strong or weak contrasts or in the case of low brightness in the field of view, image information that is adjusted with regard to its brightness can be projected into the eye in order to allow improved visual acuity.

Helmets

The integration of the information system in accordance with the invention into a fireman's helmet was described above. Similar embodiments, e.g. as a soldier's, driver's, crane operator's, sportsman's or pilot's helmet or spectacles are equally conceivable.

A soldier's helmet/spectacles on the basis of the information system in accordance with the invention could be of aid to the soldier, for example, for orientation and/or for targeting. In such case, the information apparatus of the information system preferably comprises sensors and/or radio receivers that allow an extrasensory perception of the surroundings and/or the reception of information from a command center. The output apparatus will provide information preferably visually, acoustically or tactually, e.g. in the form of short electric stimulating currents on the skin. Latter could be used to directly inform a soldier of the direction of a foreign object approaching from behind.

As a night vision device, the information system would also capture infrared light from the field of view in addition to the capture of visible light from the field of view. As described above, image information can be obtained from such captured infrared light and be employed in the enhancement of image information to be projected into the eye.

If the information apparatus comprises e.g. a GPS receiver, then the helmet could project position information or orientation aids onto the retina. Preferably, the projection of such information into the eye is carried out similar to the projection of an electronic newspaper. This means that a distraction of the soldier is avoided in that the image of the information appears to be fixed in space or vis-à-vis a neutral position of the eye. An adaptation of the image information to the background perceived therebehind for the sake of best possible readability also takes place via an evaluation apparatus belonging to the information apparatus.

Although a radio transmission or other data transmission from the soldier to a command center is generally to be avoided from strategic reasons of camouflage, a transmission of field-of-view data correlated to the eye movements of the soldier to a command center could also be meaningful in particular cases.

In an embodiment that is particular interesting for soldiers, the information apparatus comprises one or more cameras that capture images from outside the field of view. The image information obtained in this manner is then projected onto the retina via a projection apparatus. The supplementary image projected onto the field-of-view image could be projected, for example, as an image within an image as a small image in the corner of the natural or projected field-of-view image or appear as a longitudinal strip along the bottom edge. In this case, the capture of signals from the eye serves, together with the capture of the field of view, to maintain the projected images in correlation with the movements of the eye.

For a crane operator, it would be equally helpful to project in supplementary images from other perspectives into the field of view. The information system in accordance with the invention could just as well comprise supplementary sensors, with whose aid distance or weight information is determined in order to be projected into the field of view. Such information could be provided audibly or visually, e.g. upon gazing at the load in combination with the clicking of a button. In this case, the light determined from the field of view serves as a basis for the image recognition, whereas the signals from the eye allow a correlation of the captured field of view to the visual axis as described above.

The information system in accordance with the invention could provide a pilot with many various types of information. Via a connection to the information system of an airplane, relevant data such as flight altitude, speed or direction of flight or even an artificial horizon could be blended in to the pilot's field of view, for example, as described above. During landing, landing aid information could also be blended in that depict a virtual landing corridor or indicate altitude or direction correction values. In military applications, friend/foe and targeting aid information could be provided to the pilot. In this case, the gaze direction of the pilot plays a role both during the spatial blending in of the information as well as during information selection. The pilot would like a flying object upon which he has fixed his eyes' gaze to be identified. If the identification is carried out visually, he does not want the blending in to cover any relevant areas of his field of view. In this case, due consideration must be given to the contrary requirements that the relevant regions of the field of view are typically imaged onto the fovea centralis but also that only those images that are projected onto the fovea centralis are sharply imaged. Thus, an intelligent blending in must be carried out in which the relevant regions of the field of view are recognized, for example, via image recognition and not solely via the orientation of the fovea centralis. In this respect, the information system in accordance with the invention can also act as a sub-system to the information system of the aircraft and provide information thereto. In this manner, e.g. information with regard to where the pilot is looking could be supplied to the aircraft information system by the information system in accordance with the invention and contribute thereto target capturing. In true action, the information system could locate enemy radar positions via sensors and depict their position together with the associated landscape in three dimensions.

Various types of information could be provided to sportsmen via the information system in accordance with the invention as in the examples above. Orientation aids, speed information and/or enhanced field-of-view information that allows better vision at dusk, at night, in rainy spray or fog could be provided, for example, by means of a projection of information into the eye. A non-visual provision of the information is particularly suitable in the case of low-content information. Similar to the above examples, an information system in accordance with the invention worn by a sportsman could act as a sub-system of a sporting device or of a vehicle.

Pure Information Systems

Extrasensory perception can be achieved via embodiments of the information system in accordance with the invention in which the information apparatus comprises one or more sensors, e.g. magnetic field detectors, pressure sensors, thermometers, spectral sensors, optical or acoustic interference measuring devices. In particular in the case of a superimposition of a pictorial presentation of information obtained from the sensors onto the natural field of view via projection into the eye, the presentation corresponds to the needs of the person having vision. In such a case, the information system in accordance with the invention can appear as a component, in particular as a presentation apparatus, of a complex measuring apparatus.

An example of such a system is a spectacle system equipped with sensitive magnetic sensors that is in a position to locate current-conducting or metallic objects in correlation to the spectacles. If such located objects are designated, true to their position and in color, in the natural field of view by means of a projection as described above, then e.g. water pipes or electric wiring running under plaster could be very easily located. A handyman wearing such a spectacle system would see the path of the piping/wiring "painted on the wall" so to say.

If a two or three dimensional array or other one or multi-dimensional distribution of the sensors is chosen, then even e.g. highly complex vector fields or gradients could be made visible to an observer as an image over the object or arrangement associated therewith. For example, an arrangement of pressure sensors around a test object in a wind tunnel could supply pressure information that is prepared, in such a manner, via the information system in accordance with the invention as described above and projected into the eyes of an observer who is observing the test object through a window such that he sees the pressure gradients resulting from the test object there where they are present based on appropriate, colored depiction of the pressure values. Temperature information obtained by means of an infrared camera could be presented to a welder in his field of view such that the local surface temperature along the work piece is recognizable.

Similarly, spectral sensors could be used to give a user information about exact color values or material compositions. In this case, it is also practical to present the determined information audibly depending on exactly where the user is looking. In conjunction with a databank and pattern recognition, such a system could be used, for example, to at least approximately identify mushrooms or plants, wherein the user, upon system request, looks at particular parts of the mushroom/plant and/or turns these to face the sensors.

SUMMARY

In the following, based on feature groups, the essential points are again summarized that respectively characterize the invention in a particular manner either alone or in combination with one another:
1. An information system comprising
   a signal capturing apparatus that captures signals reflected back from an eye comprising a retina;
   a field-of-view capturing apparatus that captures visible light from a field of view associated with the retina without capturing a retinal reflex image of the retina;
   an information apparatus; and
   a output apparatus that provides information in cooperation with the information apparatus as a function of the captured light and in correlation with the captured signals.
2. The information system in accordance with item 1, wherein the information apparatus comprises an evaluation apparatus that obtains image information with regard to the field of view from the captured light; and
   the output apparatus comprises a projection apparatus that projects the image information onto the retina in correlation with the captured signals such that a naturally perceived field of view and the projected image information are perceived as a unitary image by the retina.
3. The information system in accordance with one of the preceding items, wherein said function encompasses a temporal or spatial correlation between the provision of the information and the captured light.
4. The information system in accordance with one of the preceding items, wherein said function encompasses a pattern recognition that yields at least one information key, and the information keys serve for an information query based on the information apparatus.
5. The information system in accordance with one of the preceding items, wherein the signal capturing apparatus comprises a scanning apparatus that records an at least partial capture of the retinal reflex image in a first scan operation and carries out a less comprehensive capture of the retinal reflex image in a later scan operation.
6. The information system in accordance with one of items 1-4, wherein the signal capturing apparatus captures the retinal reflex image only partially or not at all.
7. The information system in accordance with one of the preceding items, wherein the field-of-view capturing apparatus comprises a spherical or spherical-acting reflection layer that deflects a portion of the light directed at the eye into a sensor apparatus for capture.
8. The information system in accordance with one of the preceding items, wherein the field-of-view capturing apparatus and/or the signal capturing apparatus at least partially captures the corneal reflex image of the eye.
9. The information system in accordance with one of the preceding items, wherein the signal capturing apparatus and the field-of-view capturing apparatus are embodied as a portable unit.
10. The information system in accordance with one of the preceding items, wherein the output apparatus provides the information tactually, visually, audibly, smellably and/or tastably.
11. The information system in accordance with one of the preceding items, wherein the information apparatus a databank, a sensor system, an information network connection and/or an evaluation apparatus.
12. The information system in accordance with one of the preceding items, wherein the information system is embodied in portable form.
13. A method for providing information comprising the steps of:
   capturing signals that have been reflected back from an eye comprising a retina;
   capturing visible light from a field of view associated with the retina without capturing a retinal reflex image of the retina; and
   providing the information in cooperation with an information apparatus as a function of the captured light and in correlation with the captured signals.
14. The method in accordance with item 13, with the steps of:
   obtaining image information with regard to the field of view from the captured light; and
   projection of the image information onto the retina in correlation with the captured signals such that a naturally perceived field of view and the projected image information are perceived as a unitary image by the retina.
15. The method in accordance with item 13 or 14, wherein said function encompasses a temporal or spatial correlation between the provision of the information and the captured light.
16. The method in accordance with one of items 13-15, wherein said function encompasses a pattern recognition that yields at least one information key, and the information keys serve for an information query based on the information apparatus.
17. The method in accordance with one of items 13-15, wherein the capturing of signals comprises scan operations, wherein an at least partial capture of the retinal reflex image is carried out in a first scan operation and a less comprehensive capture of the retinal reflex image is carried out in a later scan operation.
18. The method in accordance with one of items 13-15, wherein the signal capturing captures the retinal reflex image only partially or not at all.
19. The method in accordance with one of items 13-15, wherein the capture of visible light is carried out via a spherical or spherical-acting reflection layer that deflects a portion of the light directed at the eye into a sensor apparatus for capture.
20. The method in accordance with one of items 13-15, wherein the capture of visible light and/or the signal capturing comprises an at least partially capture of the corneal reflex image of the eye.

21. The method in accordance with one of items 13-15, wherein the provision of information provides tactually, visually, audibly, smellably and/or tastably.
22. The method in accordance with one of items 13-15, wherein the information apparatus a databank, a sensor system, an information network connection and/or an evaluation apparatus.
23. A method for transferring optical information onto the human retina using a preferably serially operating scan system that captures an image falling onto the retina and an information projection system, wherein the detection and projection beam exhibits a predetermined motional pattern and wherein the information preferably depends on the signals of the scan system, characterized in that the projection operation occurs while the detection operation is running.
24. The method of item 23, wherein a partial projection operation runs after a partial detection of the image.
25. An apparatus for carrying out the method of item 23 or 24, having a preferably serially operating scan system, with which an image falling onto the retina can be captured, and having an information projection system, wherein the detection and projection beam is controllable via a control set-up in accordance with a predetermined motional pattern, characterized by a set-up that allows the projection operation while the detection operation is running.
26. An apparatus for transferring optical information onto the human retina using a serially operating scan and projection system having a predetermined motional pattern of the detection and projection beam, wherein the beam (846) of the projected light lags behind the beam (843) of the captured light.
27. The apparatus of item 26, wherein the minimal temporal displacement between capture and projection of a pixel essentially corresponds to the processing time of the previously captured image signal.
28. The apparatus of item 26 or 27, wherein the scan and projection system have a common or different beam path.
29. The apparatus of item 26 for transferring optical information onto the human retina using a serially operating scan and projection system having a predetermined motional pattern of the detection and projection beam, characterized in that the motional pattern (1502a, 1502b) of the detection beam and the projection beam are displaced from one another.
30. The apparatus of item 29, wherein the motional pattern of the detection beam and the projection beam are displaced from one another by a predetermined, small angle.
31. The apparatus of item 29, wherein the motional pattern of the detection beam and the projection beam are radially displaced from one another by a predetermined, small distance (11VA).
32. The apparatus of one of the preceding items, wherein the scan system and the detection system have separate beam paths.
33. The apparatus of one of the preceding items, wherein the scan system detects the image falling onto the retina at a location (929) of the optical system, said location being prior to the retina.
34. The apparatus of one of the preceding items, wherein the motional pattern of the detection and projection beam corresponds to a spiral.
35. The apparatus of one of the preceding items, wherein the motional pattern of the detection and projection beam corresponds to a circular or elliptical scan.
36. The apparatus of one of the preceding items, employing a constant scan velocity, or a constant angular velocity of the detection or projection beam, or a velocity adapted to the density of the receptors in the human eye, such that the receptors scanned over by the projection beam per unit of time is essentially constant.

The invention claimed is:

1. An information system comprising:
   a signal capturing apparatus that captures signals reflected back from an eye comprising a retina;
   a field-of-view capturing apparatus that captures visible light from a field of view associated with the retina without capturing a retinal reflex image of the retina;
   an information apparatus; and
   an output apparatus that provides information in cooperation with the information apparatus as a function of the captured light and in correlation with the captured signals, wherein
   the information apparatus comprises an evaluation apparatus that obtains image information with regard to the field of view from the captured light; and
   the output apparatus comprises a projection apparatus that projects the image information onto the retina in correlation with the captured signals such that a naturally perceived field of view and the projected image information are perceived as a unitary image by the retina.
2. The information system in accordance with claim 1, wherein said function encompasses a temporal or spatial correlation between the provision of the information and the captured light.
3. The information system in accordance with claim 1, wherein said function encompasses a pattern recognition that yields at least one information key, and the information keys serve for an information query based on the information apparatus.
4. The information system in accordance with claim 1, wherein the signal capturing apparatus comprises a scanning apparatus that records an at least partial capture of the retinal reflex image in a first scan operation and carries out a less comprehensive capture of the retinal reflex image in a later scan operation.
5. The information system in accordance with claim 1, wherein the signal capturing apparatus captures the retinal reflex image only partially or not at all.
6. The information system in accordance with claim 1, wherein the field-of-view capturing apparatus and/or the signal capturing apparatus at least partially captures the corneal reflex image of the eye.
7. The information system in accordance with claim 1, wherein the output apparatus provides the information tactually, visually, audibly, smellably and/or tastably.
8. The information system in accordance with claim 1, wherein the information apparatus comprises at least one of a databank, a sensor system, an information network connection and/or an evaluation apparatus.
9. A method for providing information comprising the steps of:
   capturing signals that have been reflected back from an eye comprising a retina;
   capturing visible light from a field of view associated with the retina without capturing a retinal reflex image of the retina;
   providing information in cooperation with an information apparatus as a function of the captured light and in correlation with the captured signals;
   obtaining image information with regard to the field of view from the captured light; and
   projecting the image information onto the retina in correlation with the captured signals such that a naturally perceived field of view and the projected image information are perceived as a unitary image by the retina.

10. The method in accordance with claim 9, wherein said function encompasses a temporal or spatial correlation between the provision of the information and the captured light.

11. The method in accordance with claim 9, wherein:
said function encompasses a pattern recognition that yields at least one information key; and
the at least one information key serves for an information query based on the information apparatus.

12. The method in accordance with claim 9, wherein:
the capturing of signals comprises scan operations; and
at least partial capture of the retinal reflex image is carried out in a first scan operation, with a less comprehensive capture of the retinal reflex image being carried out in a later scan operation.

13. The method in accordance with claim 9, wherein the signal capturing captures the retinal reflex image only partially or not at all.

14. The method in accordance with claim 9, wherein, the capturing of visible light and/or the signal capturing comprises an at least partial capture of the corneal reflex image of the eye.

15. The method in accordance with claim 9, wherein the provision of information is effected tactually, visually, audibly, smellably and/or tastably.

16. The method in accordance with claim 9, wherein the information apparatus comprises a databank, a sensor system, an information network connection and/or an evaluation apparatus.

* * * * *